US009345776B2

(12) United States Patent
Bowden et al.

(10) Patent No.: US 9,345,776 B2
(45) Date of Patent: May 24, 2016

(54) BIODEGRADABLE POLYMERS WITH SULFENAMIDE BONDS FOR DRUG DELIVERY APPLICATIONS

(75) Inventors: Ned B. Bowden, Riverside, IA (US); Denison J. Kuruvilla, Iowa City, IA (US); Aliasger K. Salem, Coralville, IA (US); Jun Yoo, Seoul (KR)

(73) Assignee: The University of Iowa Research Foundation, Iowa City, IA (US)

( * ) Notice: Subject to any disclaimer, the term of this patent is extended or adjusted under 35 U.S.C. 154(b) by 263 days.

(21) Appl. No.: 13/984,228

(22) PCT Filed: Feb. 10, 2012

(86) PCT No.: PCT/US2012/024734
§ 371 (c)(1),
(2), (4) Date: Dec. 18, 2013

(87) PCT Pub. No.: WO2012/115806
PCT Pub. Date: Aug. 30, 2012

(65) Prior Publication Data
US 2014/0099506 A1    Apr. 10, 2014

Related U.S. Application Data

(60) Provisional application No. 61/446,167, filed on Feb. 24, 2011.

(51) Int. Cl.
| | |
|---|---|
| A61K 47/34 | (2006.01) |
| C08G 75/30 | (2006.01) |
| C08G 73/00 | (2006.01) |

(52) U.S. Cl.
CPC ............... *A61K 47/34* (2013.01); *C08G 73/00* (2013.01); *C08G 75/30* (2013.01); *Y10T 428/2982* (2015.01)

(58) Field of Classification Search
USPC .......................... 428/402; 528/322, 373, 374
See application file for complete search history.

(56) References Cited

PUBLICATIONS

V.A. Sergeev et al: 11 Sulphur-Containing Polyarylenequinodiimides, Journal of Polymer Science, Part A: Polymer Chemistry vol. 26, 1125-1141, pp. 1125-1141, XP55028234, DOI : DOI: 10.1002/pola .1988.080260414 Retrieved from the Internet: URL:http://onlinelibrary.wiley.comj doi/10.1002/pola.1988 .080260414/pdf [retrieved on May 25, 2012].
David N. Nguyen et al: "Polymeric Materials for Gene Delivery and DNA Vaccination", Advanced Materials, vol. 21, No. 8, pp. 847-867, XP55028240, ISSN: 0935-9648, DOI:10.1002/adma.200801478.
International Search Report and Written Opinion of the International Search Authority mailed Jun. 6, 2012 for International Application No. PCT/US2012/024734.
Anderson, D.G., Nurdick, J.A., Langer, R., (2004) Materials science: Smart biomaterials, Science 305:1923-1924.
Arima, H., Motoyama, K., (2009) Recent findings concerning PAMAM dendrimer conjugates with cyclodextrins as aarriers of DNA and RNA, Sensors 9:6346-6361.
Branchaud, B.P.,(1983) Studies on the preparation and reactions of tritylsulfenimines, J. Org. Chem. 48:3531-3538.
Buncel, E, Um, I.-H., (2004) The α-effect and its modulation by solvent, Tetrahedron 60:7801-7825.
Ciuffarin, E., Gambarotta, S., Isola, M., Senatore, L, (1978) Chemistry of sulphenates in acidic media, J. C. S. Perkin II 554-557.
Craine, L., Raban, M., (1989) The chemistry of sulfenamides, Chem. Rev. 89 (4):689-712.
Elfinger, M., Uezguen, S., Rudolph, C., (2008) Nanocarriers for gene delivery—polymer structure, targeting ligands, and controlled-release devices, Curr. Nanoscience 4:322-353.
Freeman, F., Angeletakis, C. N., Maricich, T. J., (1982) 1H NMR and 13C NMR spectra of Disulfides, Thiosulfinates and Thiosulfonates, Org. Magn. Reson. 17 (1):53-58.
Freeman, F., Keindl, M. C., (1983) A facile synthesis of symmetrical alkanesulfonothioic S-alkyl esters (S-alkyl alkanethiosulfonates), Synthesis 913-915.
Freeman, F., Angeletakis, C. N., (1982) Carbon-13 nuclear magnetic resonance study of the conformations of disulfides and their oxide derivatives, J. Org. Chem. 47 (22):4194-4200.
Freeman, F., Kodera, Y., (1995) Garlic chemistry: stability of S-(2-propenyl) 2-propene-1-sulfinothioate (allicin) in blood, solvents, and simulated physiological fluids, J. Agric. Food Chem. 43:2332-2338.
Gaucher, G., Marchessault, R.H., Leroux, J.-C., (2010) Polyester-based micelles and nanoparticles for the parenteral delivery of taxanes, J. Controlled Release 143:2-12.
Green, J.J., Langer, R, Anderson, D.G., (2008) A combinatorial polymer library approach yields insight into nonviral gene delivery, Accts. Chem. Res. 41 (6):749-759.

(Continued)

*Primary Examiner* — Alicia Chevalier
*Assistant Examiner* — Elaine M Vazquez
(74) *Attorney, Agent, or Firm* — Klintworth and Rozenblat IP LLC

(57) ABSTRACT

The present invention provides methods for preparing polysulfenamides having a repeating unit of formula (4):

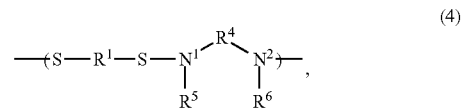

wherein $R^1$ is selected from the group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. Each of $R^4$, $R^5$ and $R^6$ are independently selected from the group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. Microparticles comprising polysulfenamides can be used as delivery vehicles for a variety of biological applications.

20 Claims, 6 Drawing Sheets

(56) References Cited

PUBLICATIONS

Guarino, V.R., Karunaratne, V., Stella, V.J., (2007) Sulfenamides as prodrugs of NH-acidic compounds: A new prodrug option for the amide bond, Bioorg. Med. Chem. Lett. 17:4910-4913.

Guo, R., A. G. Talma, R. N. Datta, W. K. Dierkes, J. W. M. Noordermeer, (2008) Solubility study of curatives in various rubbers, Eur. Poly. J. 44:3890-3893.

Hemenway, J.N., Nti-Addae, K., Guarino, V.R., Stella, V.J., (2007) Preparation, characterization, and in vivo conversion of new water-soluble sulfenamide prodrugs of carbamazepine, Bioorg. Med. Chem. Lett. 17:6629-6632.

Henke, A.; Srogl, J., (2008) Thioimides: new reagents for effective synthesis of thiolesters from carboxylic acids, J. Org. Chem. 73, 7783-7784.

Huynh, M. H. V., D. E. Morris, P. S. White, T. J. Meyer, (2002) Proton-Induced, Reversible Evolution of O2 from the OsIV ± Sulfoximido Complex [OsIV(tpy)(Cl)2{NS(O)-3,5-Me2C6H3}], Angew. Chem. Int. Ed. 41 (13): 2330-2333.

Huynh, M. H. V., P. S. White, T. J. Meyer, (2000) Proton-coupled electron transfer from sulfur: A S-H/S-D kinetic Isotope effect of ≥ 31.1, Angew. Chem. Int. Ed. 39 (22):4101-4104.

Jabbari, E., Lu, L., Yaszemski, M.J., (2006) Synthesis and characterization of injectable and biodegradable composites for orthopedic applications, Handbook of biodegradable polymeric materials and their applications 2:239-270.

Kice, J.L., Rogers, T.E., (1974) Mechanism of the alkaline hydrolysis of aryl thiolsulfnates and thiolsulfonates, J. Am. Chem. Soc. 96:8009-8014.

Kice, J.L., (1980) Mechanisms and reactivity in reactions of organic oxyacids of sulfur and their anhydrides, Adv. Phys. Org. Chem. 17:65-181.

Knapp, S., Darout, E., Amorelli, B., (2006) New glycomimetics: Anomeric sulfonates, sulfenamides, and sulfonamides, J. Org. Chem. 71:1380-1389.

Kohane, D.S., Langer, R., (2010) Biocompatibility and drug delivery systems, Chem. Sci. 1:441-446.

Koval, I.V., (1996) Synthesis and applications of sulfenamides, Russian Chem. Rev. 65:421-440.

Kroeze, R.J., Fielder, M.N., Govaert, L.E., Smit, T.H., (2009) Biodegradable polymers in bone tissue engineering, Materials 2:833-856.

Kwon, G.S., Furgeson, D.Y., (2007) Biodegradable polymers for drug delivery systems, Biomedical polymers:83-110.

Lee, S.S., Hughes, P., Ross, A.D., Robinson, M.R., (2010) Biodegradable implants for sustained drug release in the eye, Pharma. Research 27:2043-2053.

Lopez, M., Drilland, N., Bornaghi, L.F., Poulsen, S.-A., (2009) Synthesis of S-glycosyl primary sulfonamides, J. Org. Chem. 74:2811-2816.

Malyala, P., O'Hagan, D.T., Singh, M., (2009) Enhancing the therapeutic efficacy of CpG oligonucleotides using biodegradable microparticles, Adv. Drug Delivery Rev. 6:218-225.

Man, W.-L., W. W. Y. Lam, H-K. Kwong, S.-M. Peng, W.-T. Wong, T.-C. Lau, (2010) Reaction of a (Salen)ruthenium (VI) Nitrido Complex with Thiols. C-H Bond Activation by (Salen)ruthenium(IV) Sulfilamido Species, Inorg. Chem. 49:73-81.

Matsuo, J.-L, Kawana, A., Yamanaka, H., Mukaiyama, T., (2003) Sulfenamide-catalyzed oxidation of primary and alcohols with molecular bromine, Chem. Lett. 32 (2):182-183.

Meng, H.X., M. et al., (2010) Autonomous in vitro anticancer drug release from mesoporous silican nanoparticles by pH-sensitive nanovalves, J. Am. Chem. Soc. 132:12690-12697.

Mohanad, M., Dixon, A.S., Lim, C.S., (2010) Controlling subcellular delivery to optimize therapeutic effect, Therapeutic Del. 1:169-193.

Mukaiyama, T., J.-I. Matsuo, D. Iida, Kitagawa, (2001) Sulfenamide-catalyzed Oxidation of Primary and Secondary Alcohols with Molecular Bromine, Chem. Lett. 30:846-847.

Nagy P., Ashby, M.T., (2005) Reactive sulfur species: kinetics and mechanism of the oxidation of cystine by hypochlorous acid to give N,N'-dichlorocystine, Chem. Res. Toxicol. 18:919-923.

Nagy, P., Ashby, M.T., (2007) Reactive sulfur species: kinetics and mechanism of the hydrolysis of cysteine thiosulfinate ester, Chem. Res. Toxicol. 20:1364-1372.

Oh, K.T., Yin, H., Lee, E.S., Bae, Y.H., (2007) Polymeric nanovehicles for anticancer drugs with triggering release mechanisms, J. Mater. Chem. 17:3987-4001.

Owen, D.J. et al., (2007) Synthesis and evaluation of galactofuranosyl N,N-dialkyl sulfenamides and sulfonamides as antimycobacterial agents, Bioorg. Med. Chem. Lett. 17:2274-2277.

Peter, S.J., Miller, M.J., Yasko, A.W., Yaszemski, M.J., Mikos, A.G., (1998) Polymer concepts in tissue engineering, J. Biomed. Mater. Res. 43:422-427.

Saito, G., Swanson, J.A., Lee, K.-D., (2003) Drug delivery strategy utilizing conjugation via reversible disulfide inkages: role and site of cellular reducing activities, Adv. Drug Delivery Rev. 55:199-215.

Shi, J., et al., (2010) Nanotechnology in drug delivery and tissue engineering: from discovery to applications, Nano Lett. 10:3223-3230.

Twaites, B., de las Heras Alarcon, C., Alexander, C., (2005) Synthetic polymers as drugs and therapeutics, J. Mater. Chem. 15:441-445.

Ullman-Cullere, M. H., C. J. Foltz, (1999) Body Condition Scoring: A Rapid and Accurate Method for Assessing Health Status in Mice, Lab. Animal Sci. 49:319-323.

Vert, M., (2009) Degradable and bioresorbable polymers in surgery and pharmacology: beliefs and facts, J. Mater. Sci.: Mater. Med. 20:437-446.

Williams, C.K., (2007) Synthesis of functionalized biodegradable polyesters, Chem. Soc. Rev. 36:1573-1580.

Yoo et al., (2012) New Class of Biodegradable Polymers Formed from Reactions of an Inorganic Functional Group, Macromolecules 45:2292-2300.

Zhang, X. Q., C. E. Dahle, G. J. Weiner, A. K. Salem, (2007) A Comparative Study of the Antigen-Specific Immune Response Induced by Co-Delivery of CpG ODN and Antigen Using Fusion Molecules or Biodegradable Microparticles, J. Pharmaceutical Sci. 96 (12):3283-3292.

Zhao F., W. Bi, S. Zhao, J., (2011) Influence of Crosslink Density on Mechanical Properties of Natural Rubber Vulcanizates, Macromolecular Sci. B: Physics 50:1460-1469.

BIODEGRADABLE POLYMERS WITH SULFENAMIDE BONDS FOR DRUG DELIVERY APPLICATIONS

CROSS-REFERENCE TO RELATED APPLICATIONS

The present application is the National Stage of International Application No. PCT/US12/24734, filed Feb. 10, 2012, which claims the benefit of U.S. Provisional Patent Application No. 61/446,167 filed Feb. 24, 2011.

This invention was made with government support under contract CHE-0848162 awarded by the National Science Foundation, and under contracts 1R21CA13345-01/1R21CA128414-01A2 awarded by the National Institutes of Health. The government has certain rights in the invention.

BACKGROUND

Biodegradable polymers have shown wide utility in a variety of biomedical applications ranging from sutures, scaffolds for the growth of cells, and polymeric depots that provided sustained release of therapeutic agents [1-6]. Optimal use of these materials requires their molecular and macromolecular properties be tailored to the specific application for which the material is to be used [3, 7-9]. For instance, polymeric particles loaded with drugs that are targeted to the endosomal compartments of cells should ideally be stable at physiological pH in the bloodstream, but readily break down at a lower pH to release their drug cargo in the endosome where the pH is approximately 4 to 5 [10-13].

Biodegradable polymers are attractive in drug delivery applications because polymeric particles injected in vivo can accumulate in several organs including the liver, spleen, lungs and heart and often result in toxic side effects if they do not break apart into smaller, easily excretable side products [14, 15]. The degradation of these polymers is also one of the mechanisms by which controlled release of drugs and other therapeutics is achieved. Most synthetic polymers in biomedical applications are polyesters, polyamides, polyanhydrides, or polymers featuring two or more of the ester, amide, and anhydride groups. Ideally, such polymers degrade to short polymers or small molecules at reasonable times without the use of enzymes [16-18]. Thus, these polymers can be excreted from the body before toxic side-effects occur.

Moreover, microparticles containing a drug should be stable in the bloodstream where the pH is 7.4; however, when they are endocytosed into a cell they should break down rapidly in the endosome/lysosome where the pH is approximately 4 to 5. Another challenge in the field of drug delivery via synthetic polymers is the need to fabricate "smart" delivery vehicles that target selected cells. Targeting of cells is most commonly done by placing ligands on the surface of the microparticles that are recognized by selected cells. The most common biodegradable polymer used in drug delivery applications is poly(lactic-co-glycolic acid), but this polymer lacks reactive surface functional groups that can be functionalized to expose ligands to direct attachment to cells.

It can be very challenging to design a polymer with a new functional group along its backbone that renders it stable at physiological pH but also allows it to be degraded at reasonable time scales in the body without toxic side effects. The introduction of a new functional group that can be used to synthesize biopolymers has the potential to open up new applications in this field and will allow more complex, potentially "smart" drug delivery vehicles to be synthesized [7, 11, 17].

Sulfenamides are an understudied inorganic functional group with the general formula of RS—NR' that are used as protecting groups for amines (typically as (Ph$_3$C)S—NR') [44], vulcanizing agents in the rubber industry [45], in the activation of C—H bonds [46], as ligands on metals to promote oxygen atom transfer [47], as intermediates in the synthesis of sulfenamides [48], as oxidants for alcohols [49], and as ligands in the synthesis of inorganic coordination compounds.[50, 51]. Although sulfenamides are well studied in small molecule synthesis, no examples of polysulfenamides are known.

FIGURES

DEFINITIONS

Figure 1:
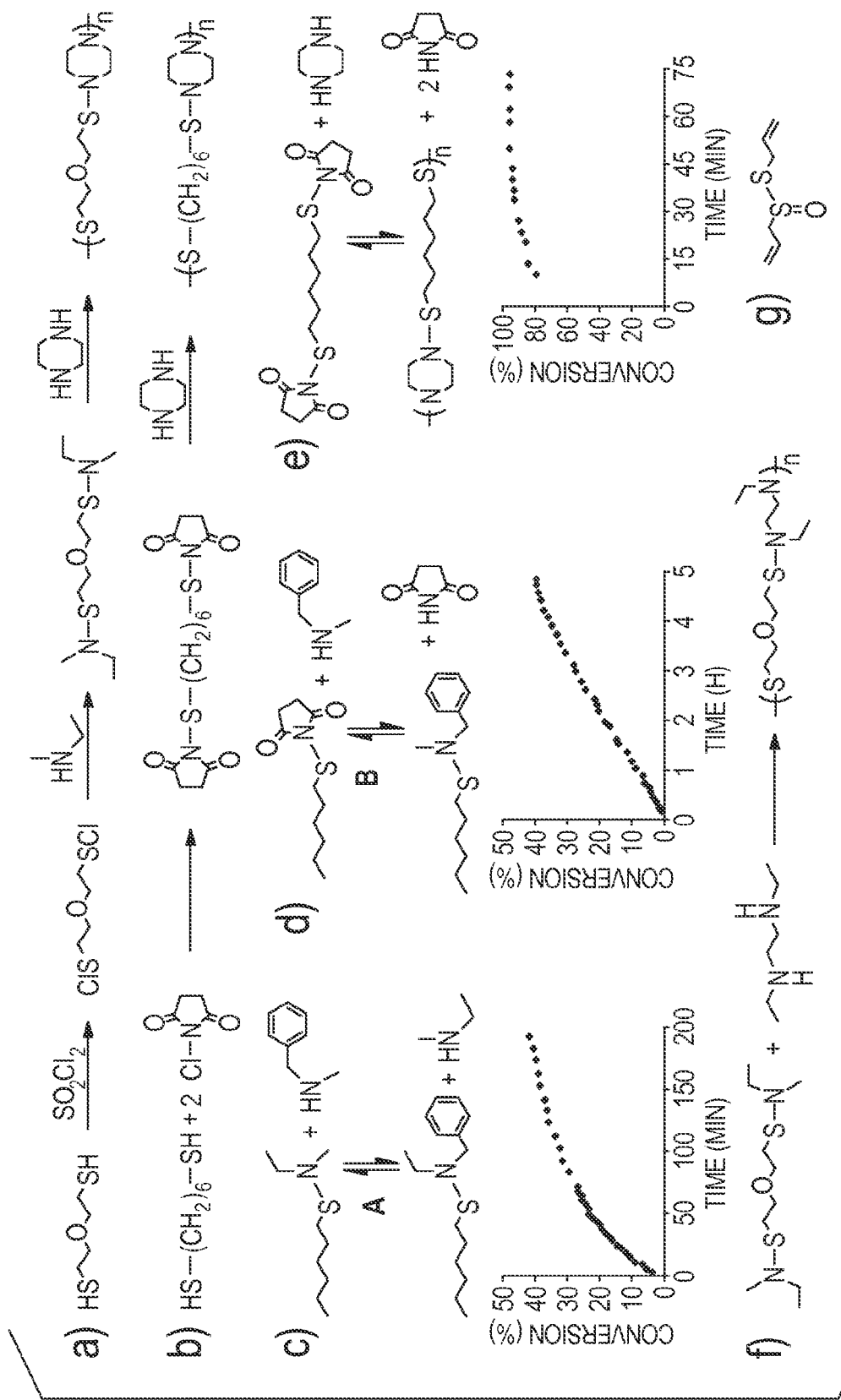
FIG. 1 illustrates synthetic schemes for the polymers of the invention and the results of kinetic studies.

As used herein, the terms "di-sulfenyl chloride" and "disulfenyl chloride" refer to a molecule of formula Cl—S—R$^1$—S—Cl, wherein R$^1$ is as defined hereinbelow.

As used herein, the term "diamine" refers to a molecule comprising at least two amine moieties. A secondary diamine is a diamine wherein both of the amine moieties are secondary amines.

As used herein, the term "polymer" refers to a molecule comprising at least five repeating units. For example, a PET polyester comprises at least five repeating units, wherein each unit is of formula —OC—C$_6$H$_4$—COO—CH$_2$—CH$_2$—O—.

As used herein, the term "microparticles" refers to particles having an average size of between 0.1 μm and 100 μm.

As used herein, the terms "imide" refers to a molecule having an "imidyl group," that is a group having two carbonyl groups bound to a nitrogen atom.

DETAILED DESCRIPTION

The present invention is based on the discovery of the first synthesis of polysulfenamides, i.e. polymers comprising sulfenamide functional groups. The product polymers were shown to be stable in aprotic solvents and in protic solvents under neutral conditions. Importantly, the polysulfenamides were mostly stable at pH of 7.4 but rapidly degraded under acidic conditions typical of the endosome/lysosome. The polysulfenamides were fabricated into microparticles loaded with fluorescent dye that were internalized into cells with minimal toxicity. In addition, the microparticles showed no in vivo adverse effect when injected in mice. The microparticles are biocompatible, biodegradable, and able to be loaded with a drug and taken into cells. The particles are also able to be functionalized on their surface to attach molecules that can be used as ligands to target certain cell lines.

This functionalization can be achieved through transamination of surface sulfenamides bonds exposed on the surface of microparticles. The sulfenamide bond reacts with amines to yield new sulfenamides (RSNR$^X$+HNR$^Y$→RSNR$^Y$+HNR$^X$) and provides a route to attaching ligands to the surface of microparticles. Furthermore, the sulfenamides degrade into different products than esters, amides, anhydrides, and other polymers. Such new products of degradation may provide routes to address the toxicities found for most other synthetic polymers.

In a first aspect, the present invention provides a first method for synthesizing polysulfenamides. In this first method, a disulfenamide is reacted with a diamine, to yield a polysulfenamide. Preferred disulfenamides are those of formula (1):

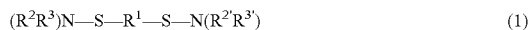

$R^1$ is selected from the group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. More preferably, $R^1$ is selected from the group consisting of alkyl, cycloalkyl, ether, and cycloether. Most preferably, $R^1$ is selected from the group consisting of alkyl and ether. $R^2$, $R^3$, $R^{2'}$, and $R^{3'}$ are preferably each independently selected from the group consisting of hydrogen, alkyl, alkenyl, alkynyl, haloalkyl, alkoxyalkyl, hydroxyalkyl, cycloalkyl, ether, aryl, and heteroaryl. More preferably, $R^2$, $R^3$, $R^{2'}$, and $R^{3'}$ are each independently selected from the group consisting of hydrogen, alkyl, and cycloalkyl. Moreover, $R^2$ and $R^3$ may both belong to the same cyclical moiety. Similarly, both $R^{2'}$ and $R^{3'}$ may also belong to a cyclical moiety.

The disulfenamides are reacted with diamines, to yield polysulfenamides. The diamines are preferably secondary diamines. Preferred secondary diamines are those of Formula (2):

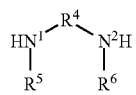

Each or $R^4$, $R^5$, and $R^6$ are independently selected from the group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. More preferably, each of $R^4$, $R^5$, and $R^6$ are independently selected from the group consisting of alkyl and ether. Most preferably, $R^4$, $R^5$, and $R^6$ are all alkyl. As apparent in formula (2), moiety $R^4$ is covalently linked to both nitrogen atoms $N^1$ and $N^2$. Optionally, $R^5$ is covalently linked to $R^6$, thereby forming a cyclical moiety comprising $N^1$, $N^2$, $R^4$, $R^5$, and $R^6$. Also optionally, either or both of moieties $R^5$ and $R^6$ are covalently linked to $R^4$. Preferably, the diamine is a cyclic diamine, such as piperazine.

In an exemplary embodiment of this first aspect of the invention, the polysulfenamide may be synthesized based on reaction scheme (I):

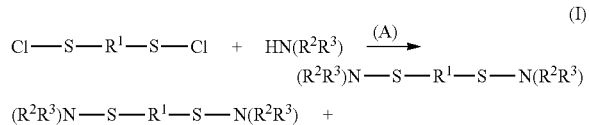

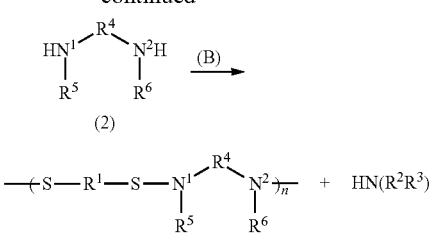

Wherein n is a natural number of at least 5. Di-sulfenyl chloride Cl—S—R$^1$—S—Cl may be prepared in situ by chlorinating a dithiol of formula H—S—R$^1$—S—H, for example by contacting with Cl$_2$ or with a chlorinating agent such as SO$_2$Cl$_2$. Transamination reaction (B) is preferably carried out in a mixture comprising an aprotic solvent. More preferably, the mixture comprises a solvent comprising at least one halogen atom. Yet more preferably, the mixture comprises one or more of CH$_2$Cl$_2$, CHCl$_3$, and CCl$_4$.

In a second aspect, the present invention provides a second method for synthesizing polysulfenamides, based on reacting activated dithiols with the secondary amines of the above formula (2). The activated dithiols are preferably of formula (3):

$R^1$ is selected from the group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. More preferably, $R^1$ is selected from the group consisting of alkyl, cycloalkyl, ether, and cycloether. Most preferably, $R^1$ is selected from the group consisting of alkyl and ether.

X is a leaving group which is displaced by reacting with an amine group. Preferably, X is selected from the group consisting of halogen, tosylate group, mesylate group, and imidyl group. Preferably, X is an imidyl group. More preferably, X is a succinimidyl group. The activated dithiols can be prepared, for example by reacting dithiols of formula HS—R$^1$—SH with an N-haloimide, such as N-chlorosuccinimide, N-bromosuccinimide, or N-iodosuccinimide.

In an exemplary embodiment of this second aspect of the invention, a polysulfenamide may be synthesized based on reaction scheme (II):

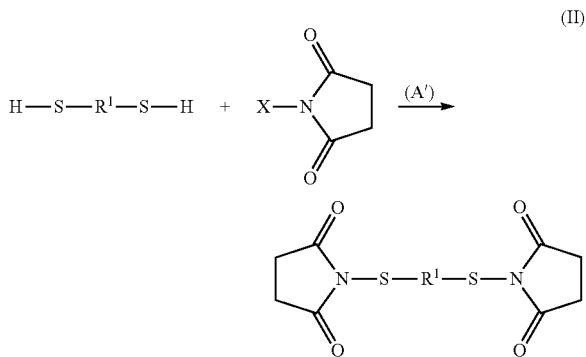

-continued

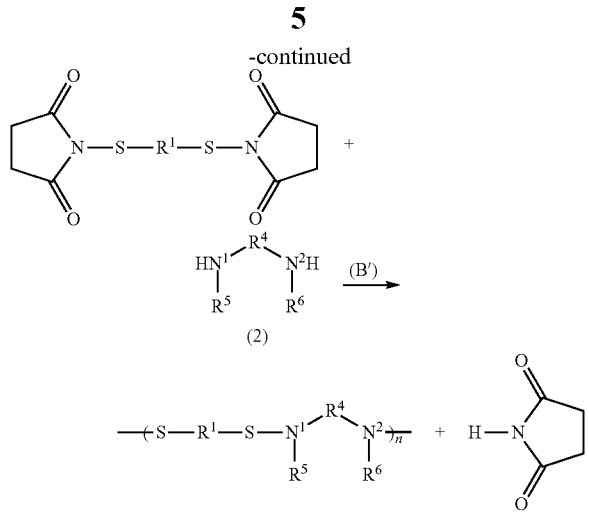

(2)

n is a natural number of at least 5. Each or $R^4$, $R^5$, and $R^6$ are independently selected from the group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. More preferably, each of $R^4$, $R^5$, and $R^6$ are independently selected from the group consisting of alkyl and ether. Most preferably, $R^4$, $R^5$, and $R^6$ are all alkyl. As apparent in formula (2), moiety $R^4$ is linked to both nitrogen atoms $N^1$ and $N^2$. Optionally, $R^5$ is linked to $R^6$, thereby forming a cyclical moiety comprising $N^1$, $N^2$, $R^4$, $R^5$, and $R^6$. Preferably, the diamine is a cyclic diamine, such as piperazine. Moiety X is a leaving group preferably selected from Cl, Br, or I, more preferably Cl.

Reaction (B') between the dithiosuccinimide and the secondary diamine (2) is preferably carried out in a mixture comprising an aprotic solvent, such as methylene chloride ($CH_2Cl_2$), chloroform ($CHCl_3$), $CCl_4$, hexane, benzene, toluene, 1,4-dioxane, diethyl ether, tetrahydrofuran, ethyl acetate, acetone, dimethylformamide, acetonitrile, and dimethyl sulfoxide. More preferably, the mixture comprises a solvent comprising at least one halogen atom. Yet more preferably, the mixture comprises one or more of $CH_2Cl_2$, $CHCl_3$, and $CCl_4$.

In a third aspect, the present invention provides polysulfenamides comprising a repeating unit of formula (4):

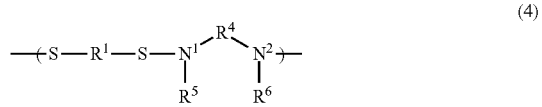

(4)

Wherein $R^1$ is selected from the group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. Each of $R^4$, $R^5$, and $R^6$ are independently selected from the group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. Preferably, $R^1$ is selected from the group consisting of alkyl, cycloalkyl, ether, and cycloether. Most preferably, $R^1$ is selected from the group consisting of alkyl and ether. Also preferably, each of $R^4$, $R^5$, and $R^6$ are independently selected from the group consisting of alkyl, cycloalkyl, ether, and cycloether. Most preferably, $R^4$, $R^5$, and $R^6$ are all alkyl. Also preferably, $R^5$ and $R^6$ are part of the same cyclic moiety. Yet more preferably, at least one of nitrogen atoms $N^1$ and $N^2$ is part of said cyclic moiety. Optionally, either or both of moieties $R^5$ and $R^6$ are covalently linked to $R^4$.

In a fourth aspect, the present invention provides microparticles comprising polysulfenamides. The particles can be made according to methods known to those of ordinary skill in the art, for example by oil-in-water (o/w) single emulsion, solvent evaporation techniques. Drugs and fluorescent molecules such as rhodamine can be incorporated into the microparticles, for example by mixing them in a polysulfenamide/chloroform mixture prior to emulsification. Preferably, the microparticles have an average size of about 0.1 μm to about 20 μm. More preferably, the average size of the microparticles is about 1 μm to about 5 μm. Yet more preferably, the average size of the microparticles is about 2 μm to about 3 μm.

The microparticles are characterized by a faster degradation rate at physiological pH (7.4) than acidic pH (4.0), and are therefore more stable in the bloodstream than inside cells. They have also been shown to be readily endocytosed, and to be located near the cytoplasm of the cell, indicating the phagocytosis of the microparticles by cells. In addition, the microparticles have shown low toxicity at even the highest concentrations. These features indicate that polysulfenamides have potential in the delivery of vaccines and growth factors, gene therapy applications, chemotherapeutics and in regenerative medicine.

Another important property of the microparticles is that they can be easily functionalized on the surface by means of simple transamination reactions with amines. This allows for the binding of any type of ligands to the microparticle surface. For example, aptamers and biological moieties can readily be conjugated to the surface and this feature can be adapted to a wide range of applications including sensing, self-assembly, and tissue engineering.

EXAMPLES

Synthesis of Polysulfenamides

In a first attempt according to the above first polysulfenamide synthesis method, dithiols were reacted with $SO_2Cl_2$ to yield molecules with S—Cl bonds that were too unstable to be isolated (FIG. 1a). Rather, these molecules were reacted with N-ethylmethylamine to yield sulfenamides in high yields. These sulfenamides were reacted with diamines to yield a polymer; the leaving group in this polymerization was N-ethylmethylamine (having a boiling point of 36-37° C.) which was removed with heat to drive the reaction to completion.

In the second polysulfenamide synthesis method, dithiols were reacted with N-chlorosuccinimide to yield dithiosuccinimides (FIG. 1b). These molecules were then reacted with diamines to yield polysulfenamides.

Simple bimolecular reactions were studied to determine the kinetics of each transamination reaction shown in FIG. 1 to determine the best conditions for the polymerization. Molecule A was synthesized and reacted with N-benzylmethylamine in $C_6D_6$, DMSO-$d_6$, and $CD_3OD$ at different temperatures (FIG. 1c). This reaction was slower in $C_6D_6$ with no conversion after 24 hours (h) at room temperature and 11% conversion after 24 h at 60° C. When DMSO-$d_6$ was used as the solvent, the conversion reached 7% after 24 h at room temperature and 32% after 24 h at 50° C. In $CD_3OD$, the kinetics were much faster at room temperature with a rate constant of $1.0 \times 10\text{-}4\ M^{-1}\ s^{-1}$ (FIG. 1c). This reaction was run in a sealed NMR tube and reached a conversion of 40% after 3 h, and at longer periods of time it reached an equilibrium mixture of 50% of each sulfenamide.

As illustrated in FIG. 1f, when the polymerization of a disulfenamide with a diamine was attempted, according to the first polysulfenamide synthesis method, the results were not promising. Although the kinetics of reaction were rapid in methanol, the resulting polymer was insoluble in methanol which indicated that this solvent may be a poor choice to conduct polymerizations. Polymerizations at high concentrations of monomers in solvent mixtures of (1/1 v/v) $CD_3OD/CDCl_3$ or (1.2/1 v/v) $CD_3OD/DMSO\text{-}d_6$ at 40° C. yielded soluble oligomers even after 3 days. This polymerization was attempted in refluxing benzene for 24 h with the reaction vented to allow N-ethylmethylamine to boil off resulting in a low yield of a modest molecular weight polymer (Mw=2,840 g mol$^{-1}$).

The reaction of a thiosuccinimide (molecule B in FIG. 1d) with N-benzylmethylamine was much faster in aprotic solvents than the same reaction between molecule A and N-benzylmethylamine. In $CD_2Cl_2$ at room temperature the reaction between molecule B and N-benzylmethylamine had a rate constant of $3 \times 10\text{-}5\ M^{-1}\ s^{-1}$ and reached 35% conversion after 4 h. Although this transamination reaction was approximately 3 times slower than the reaction between molecule A and N-benzylmethylamine in $CD_3OD$, the difference in solvent appeared to be important. Methylene chloride and chloroform were excellent solvents for both monomers and polymers, and the reaction of thiosuccinimides with secondary amines went to greater than 97% conversion at reasonable concentrations at room temperature. For instance, the polymerization reaction shown in FIG. 1e went to greater than 95% conversion within 50 min in $CDCl_3$ at room temperature. This polymerization method was used in all subsequent polymerizations.

A series of polymers were synthesized from dithiosuccinimides and secondary diamines (Table 1), according to the second polysulfenamide synthesis method. The polymerizations were completed in methylene chloride or chloroform at room temperature for 24 h. The polymers had molecular weights up to 6,300 g mol$^{-1}$ and degrees of polymerization that ranged from 90% to 97%.

TABLE 1

Synthesis of polysulfenamides.

| Entry | Composition | $M_w$ (g mol$^{-1}$)[a] | Conversion (%)[b] | PDI |
|---|---|---|---|---|
| 1 | | 3,700 | 97 | 1.42 |
| 2[c] | | 6,300 | 98 | 1.22 |
| 3[c] | | 3,700 | 97 | 1.06 |
| 4 | | 2,300 | 95 | 1.60 |
| 5[c] | | 2,900 | 96 | 1.13 |

[a] The absolute $M_w$ and PDI were measured with multi-angle laser light scattering and refractive index detectors unless otherwise noted.
[b] The conversion was calculated based on the molecular weight of the polymer and monomers according to the equation $Xn = 1/(1 - P)$
[c] The $M_w$ and PDI were measured versus polystyrene standards using a calibration curve.

Degradation of Sulfenamides in Aprotic and Protic Solvents

Prior evidence by others indicated that the S—N bond would degrade under acidic conditions with protic solvents. In fact, one challenge of working with small molecules containing sulfenamides is that they tend to degrade on acidic silica gel and poor yields are often obtained after column chromatography [25, 26]. Poor yields were obtained for sulfenamides cleaned on silica gel, but when they were cleaned by chromatography on basic aluminum oxide the isolated yields were high. Furthermore, when a small molecule with a sulfenamide bond was added to a NMR tube in $CDCl_3$ with 30 mg of silica gel, approximately 50% of it decomposed after 16 h at room temperature, but no decomposition was seen in an identical experiment in the absence of silica gel. These results indicated that polymers with sulfenamides along the backbone would decompose under acidic conditions, a result that is desirable for many applications in drug delivery.

Figure 2:
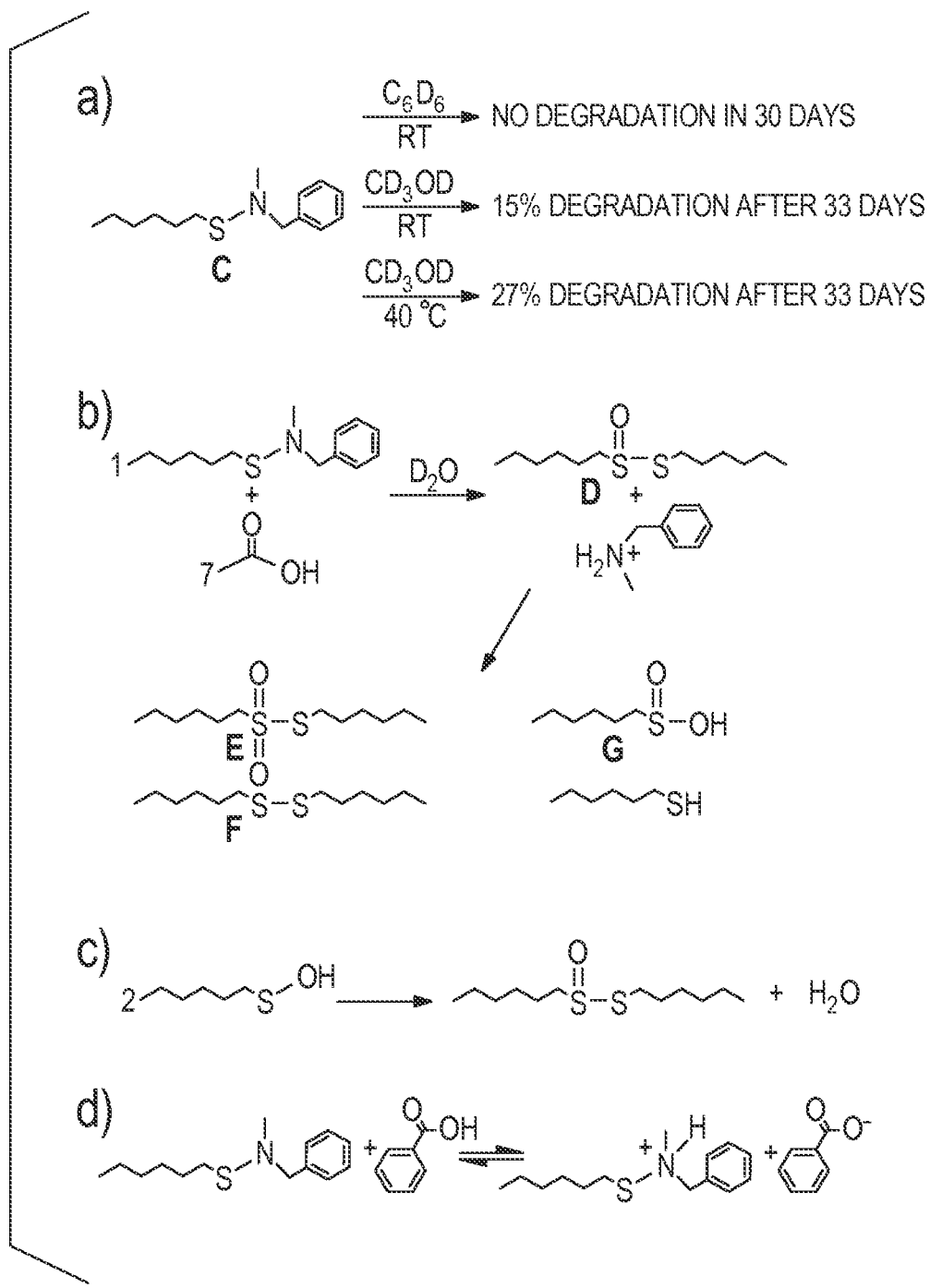
FIG. 2 illustrates degradation studies on molecules comprising sulfenamide groups.

To further study the degradation of the S—N functional group, molecule C from FIG. 2a was synthesized and studied under a variety of reaction conditions. To probe the stability of this molecule under neutral conditions, it was added to $CD_3OD$ and $C_6D_6$. After 30 days, the $^1H$ NMR spectrum of molecule C in $C_6D_6$ was unchanged, which demonstrated its stability in aprotic solvents. This molecule slowly degraded in $CD_3OD$; after 33 days 15% of it degraded at room temperature and only 27% degraded when heated to 40° C. for the same period of time. These results provided an understanding of the stability of polysulfenamides in water under neutral conditions and indicated that these polymers possess reasonable stabilities under neutral conditions in a polar, protic solvent.

The degradation of molecule C was studied under acidic conditions in $CD_3OD$ and $D_2O$ to understand how polysulfenamides would break down in the endosome of cells where the pH is approximately 4 to 5. Molecule C was not soluble in $D_2O$, so the kinetics of degradation were not studied in this solvent, but the products were isolated and characterized. Molecule C was added to $D_2O$ with seven molar equivalents of acetic acid. After 41 h the organic molecules were extracted and initially studied by $^1H$ NMR spectroscopy prior to isolation by column chromatography. The $^1H$ NMR spectrum of the extract before chromatography indicated that approximately 75% of the product was the thiosulfinate (molecule D in FIG. 2b) with the remainder mostly composed of molecules E and F.

The initial reaction of molecule C with water yielded a sulfenic acid, but sulfenic acids are transient intermediates that rapidly condense as shown in FIG. 2c [24, 27, 28]. Based on literature precedent, it is believed that molecule D further decomposed via multiple pathways to yield molecule E, molecule F, and a sulfinic acid (molecule G) [28-31]. Thiosulfinate esters such as molecule D have known oxidation states for cysteine residues and are found in natural products such as allicin (a component of garlic; FIG. 1g). As such, thiosulfinates are already present in the body and are known to decompose at reasonable rates—the half-life of the decomposition of allicin at pH=7.5 at 37° C. is approximately 2 days [8, 29].

The kinetics of degradation of molecule C were much faster with benzoic acid in $CD_3OD$ than without it. With five equivalents of benzoic acid the molecule reached 51% degradation within 4 min compared to only 15% degradation after 33 days in the absence of benzoic acid. When molecule C was exposed to two molar equivalents of p-toluenesulfonic acid (pKa <−2) or trifluoroacetic acid (pKa=0.3) in $CD_3OD$ it degraded to >90% within four minutes. Without being bound to any particular theory, it appears that the decomposition of sulfenamides is catalyzed by acid as observed in prior studies [25, 26]. During the course of these experiments, it was also noticed that benzoic acid only partially protonated the sulfenamide (FIG. 2d). This result indicated that the protonated sulfenamide had approximately the same pKa as benzoic acid (pKa of 4.2 in water) despite the typical pKa of approximately 10 for protonated amines. Without being bound to any particular theory, it is believed that the reason for the low pKa of sulfenamides was due to the α-lone pair effect which typically lowers a pKa by orders of magnitude and has been observed in other molecules such as hydrogen peroxide [32, 33].

Fabrication and Degradation of Microparticles of Polysulfenamides

Microparticles were fabricated from the polymer in entry 2 in Table 1 to study whether these polymers could form the basis of drug delivery vehicles. The microparticles were prepared using an oil-in-water single emulsion solvent evaporation methodology. In this approach, the polymer was dissolved in chloroform and then emulsified in surfactant containing water phase. The emulsion was stirred overnight until the chloroform evaporated.

Drugs and fluorescent molecules such as rhodamine could be incorporated into the microparticles by mixing them in the polymer/chloroform mixture prior to emulsification. The average size of the microparticle was 2.6 microns with a polydispersity index (PDI) of 0.62. They were spherical in shape, had a smooth surface, and had a negative charge of −41 mV in PBS buffer at pH=7.4 (FIG. 3b). Without being bound to any particular theory, the reason for the negative charge was understood in terms of prior experiments that demonstrated that sulfenamides did not appreciably protonate at pH=7.4, but they slowly degraded to yield sulfinic acids that deprotonated and led to a negatively charged surface.

Figure 3:
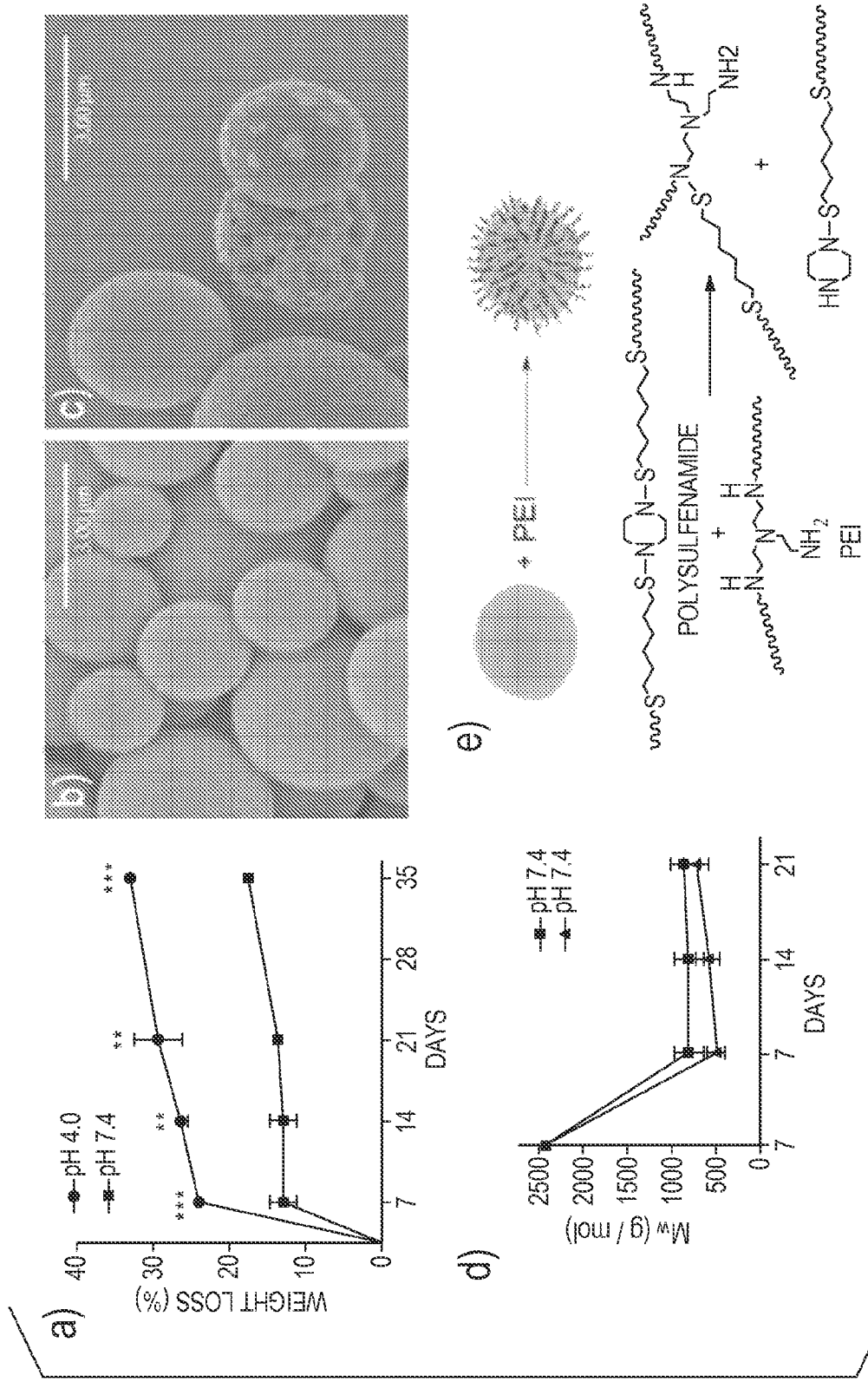
FIG. 3 illustrates particles comprising the polymers of the invention, their functionalization with PEI, and data from degradation studies carried out on the particles.

To study whether these microparticles could be functionalized by the transamination reaction shown in FIG. 1c, they were reacted with polyethylene imine in water at 4° C. for 5 h (FIG. 3). After washing with deionized water, they were collected by centrifugation and their surface charge was measured. The particles had now surface charges from 8 to 25 mV in PBS buffer at pH=7.4, which indicated that they were coated with positively charged amines. This work demonstrated the ability to functionalize the surface of the particles using simple transamination reactions with free amines.

Microparticle degradation was studied at both physiological pH (7.4) and acidic pH (4.0) to learn whether the particles would decompose over time. FIG. 3a shows the percentage weight loss of the samples at different points in time. After one week, a weight loss of 24% was observed for microparticles in acetate buffer as compared to a weight loss of 13% for particles in PBS. On day 35, the weight loss in acidic buffer was about 33% as compared to about 17% at physiological pH. Weight loss was significantly higher for particles in acetate buffer as compared to particles in PBS, indicating faster degradation of the microparticles in acidic environments. The differences in the rates of degradation at pH 7.4 and 4.0 reflected the rapid degradation of molecule C under acidic conditions in methanol and its slow degradation in methanol in the absence of acid.

As illustrated in FIG. 3c, SEM images of the acidic pH-degraded particles revealed a rough morphology of the polymer surface that was consistent with polymer degradation. Some microparticles were dissolved in chloroform at each time period and size exclusion chromatography spectra were obtained. These spectra showed that the polymer had a lower molecular weight after being degraded in water, as expected (FIG. 3d).

Uptake of Microparticles by Cells

Figure 4:
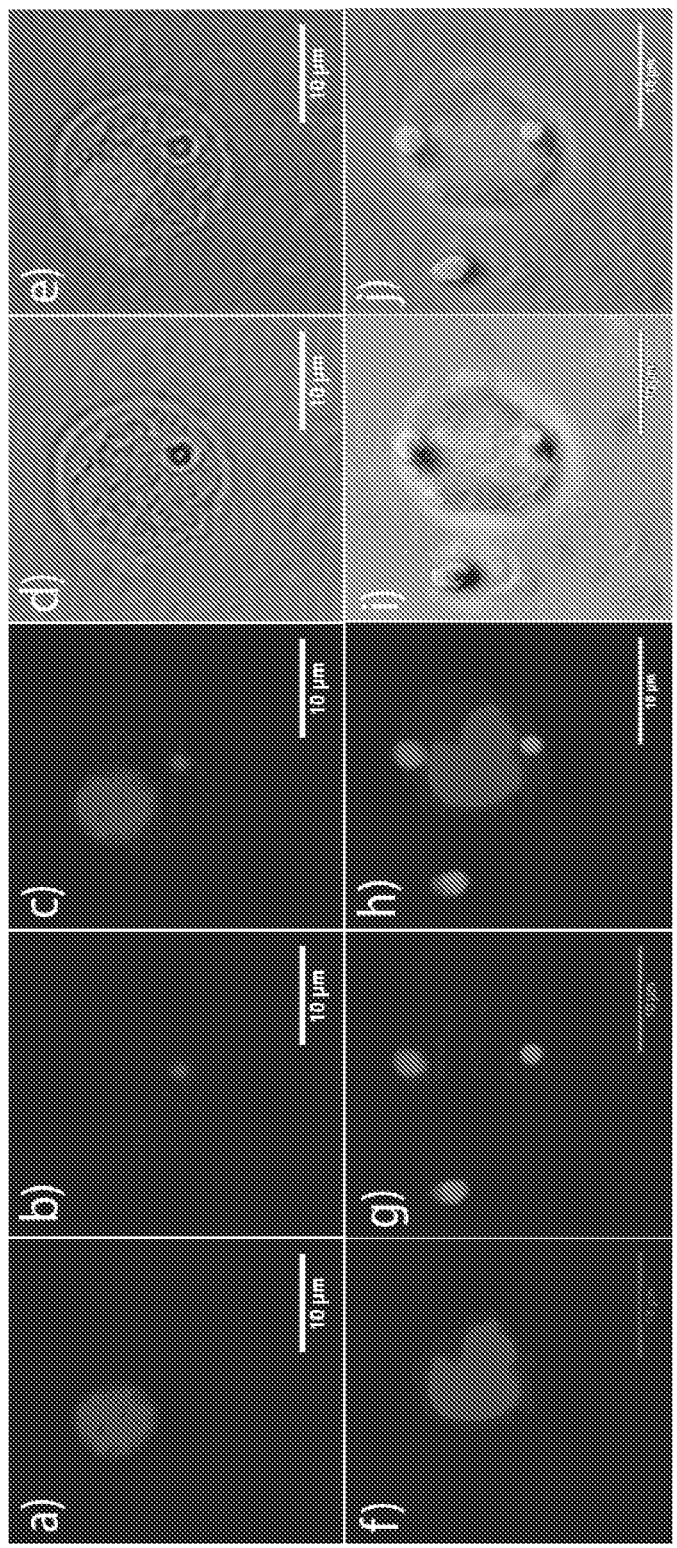
FIG. 4 illustrates the phagocytosis of the particles of the invention by living cells.

The uptake of the microparticles was studied in JAWSII and human embryonic kidney (HEK293) cells using confocal microscopy. JAWSII cells are immature dendritic cells derived from mouse bone marrow and are commonly targeted by particle based vaccines for generation of therapeutic immune responses. HEK293 cells are one of the most common cell lines used to evaluate novel gene therapies. Microparticles were loaded with rhodamine B during fabrication and were then exposed to the JAWSII and HEK293 cells. The microparticles were found to be located near the cytoplasm of the cell, indicating the phagocytosis of the microparticles by cells (FIG. 4). The uptake of microparticles by both cell lines suggests that this system has potential in immunological applications, especially in vaccine delivery and potential for gene therapy applications.

Figure 5:
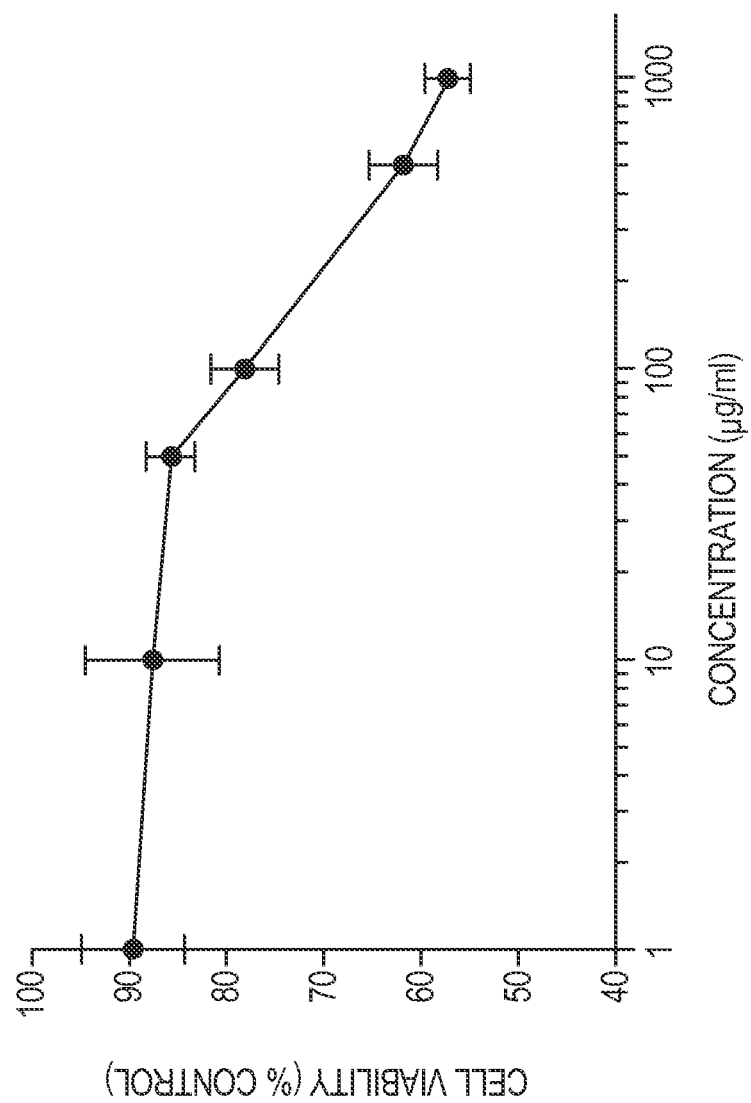
FIG. 5 illustrates the results of a study on the in vitro toxicity of particles according to the invention.

The in vitro toxicity of these microparticles was evaluated with HEK293 cells. In initial work, these cells were incubated with the microparticles at a range of concentrations of 1 microgram to 1,000 micrograms per mL of growth medium for 4 h. The cell viability was measured by standard techniques of measuring the metabolic activity of cells in a control without microparticles and the metabolic activity of cells that were exposed to the microparticles. The ratio of these concentrations was plotted as the "cell viability" in the y-axis of FIG. 5. No toxicity was observed at even the highest concentrations after 4 h, so a longer incubation time of 24 h was studied and shown in FIG. 5. At the expected working concentrations of microparticles minimal toxicity was observed. Interestingly, at the highest concentration of 1 mg of microparticles per mL of solution where the wells containing HEK293 cells were beginning to become saturated with microparticles, the cell viability was still 57%. This suggests that polysulfenamides have low toxicity and are therefore suitable for drug, gene, and vaccine delivery applications.

In Vivo Toxicity Studies

The in vivo toxicity of the polysulfenamide microparticles were evaluated in BALB/C mice. Microparticles were administered via intraperitoneal (i.p.) injection because the i.p route allows particles to enter the systemic circulation allowing for a better gauge of systemic toxicity than subcutaneous or intramuscular injection. The mice were divided into five groups and were injected with either 5 mg, 10 mg, or 15 mg of polysulfenamide microparticles from entry 2 in Table 1; 10 mg of microparticles of poly(D,L-lactide-co-glycolide) as a control group; or a sterile PBS buffer solution. The mass of particles injected in these experiments was significantly higher than the typical therapeutic mass of microparticles injected for vaccine based application. The mice were followed for 23 days and blood was drawn at 0, 2, 9, 16, and 23 days to test for the levels of liver enzymes. Specifically, alanine aminotranferease (ALT) and aspartate aminotransferase (AST) are liver enzymes (transaminases) that can be detected systemically as a result of hepatocellular damage (liver inflammation, necrosis, cellular degeneration and increased membrane permeability) and are approved FDA assays for determination of pre-clinical toxicity in new chemical entities.[52]

The in vivo study showed that the polysulfenamide microparticles did not result in any significant increase in the serum ALT and AST levels over the study period, relative to either day 0 or poly(D,L-lactide-co-glycolide) microparticles, indicating lack of any liver damage. In addition, mice were monitored daily and remained in good health as determined by the Body Condition Scoring technique.[53] No adverse injection site reactions such as infection, redness or wounding were observed. Furthermore, no mice died as a result of injections of polysulfenamide microparticles over the entire study period. In summary, the in vivo studies showed no adverse effects from the polysulfenamides.

Experimental Procedures

Materials. Phosphate buffer saline (PBS) is a product of Sigma-Aldrich (St. Louis, Mo.). Dulbecco's Modified Eagle's Medium (DMEM) was obtained from Gibco BRL (Grand Island, N.Y.). LysoTracker® Green was obtained from Invitrogen (Eugene, Oreg., USA). Paraformaldehyde (16% solution, EM grade) was obtained from electron microscopy services (Hatfield, Pa.) and Vectashield mounting medium for fluorescence with DAPI was a product of Vector laboratories (Burlingame, Calif.). 1-Hexanethiol, 1,6-hexanedithiol, 2-mercaptoethyl ether, N-benzylmethylamine, N-ethylmethylamine, N,N'-dimethyl-1,6-hexanediamine, N-chlorosuccinimide, triethylamine, ethylenediamine, benzoic acid, p-toluenesulfonic acid, acetic acid, and sulfuryl chloride were purchased from Aldrich or Acros Organics at their highest purity and used as received. HPLC grade chloroform purchased from Acros Organics was used as the GPC solvent after filtering it through a glass frit. All other solvents were reagent grade and purchased from Acros Organics. Piperazine (99%) was purchased from Aldrich. It was purified by sublimation under vacuum at 130° C. N,N'-Diethylethylenediamine (95%) was purchased from Aldrich and distilled under vacuum at 30° C. Genduran silica gel 60 (230-400 mesh) and basic alumina Brockman activity I (60-325 mesh) were purchased from Fisher Scientific and used for column chromatography.

Cell culture. Human embryonic kidney cells (HEK293) and JAWSII were obtained from American Type Culture Collection (ATCC, Rockville, Md.). HEK293 cells were maintained in DMEM supplemented with 10% fetal bovine serum (FBS) and gentamycin sulfate at 50 µg ml$^{-1}$. JAWSII were maintained in Alpha MEM with ribonucleosides, deoxyribonucleosides, 4 mM L-Glutamine, 1 mM sodium pyruvate, 5 ng/ml murine GM-CSF, and 20% fetal bovine serum (FBS). Cells were incubated at 37° C. in a humidified 5% $CO_2$-containing atmosphere.

Characterization of small molecules and polysulfenamides. $^1H$ and $^{13}C$ NMR spectra were recorded on a Bruker DPX 300 at 300 MHz and 75 MHz respectively. $CDCl_3$ was used as NMR solvent with tetramethylsilane (TMS) as an internal standard. Size exclusion chromatography (SEC) was performed using chloroform as the mobile phase (1.00 mL min$^{-1}$) at 40° C. A Waters 515 HPLC pump and two Waters columns (Styragel HR4 and HR5E) were used in series. A DAWN EOS 18 angle laser light scattering detector from Wyatt Corp. to measure light scattering and a Wyatt Optilab DSP to measure changes in refractive index were used to measure absolute molecular weights of polymers. Polystyrene standards (1,260 g mol$^{-1}$, 3,790 g mol$^{-1}$, 13,000 g mol$^{-1}$, and 30,300 g mol$^{-1}$) were used to generate a calibration curve to measure relative molecular weights of some polysulfenamides as indicated in Table 1.

Synthesis of Small Molecules and Polymers

Hexanesulfenyl chloride. Alkylsulfenyl chlorides were prepared according to a literature procedure [39]. Since they quickly returned to thiols after being exposed to air, alkylsulfenyl chlorides were used in situ for the preparation of sulfenamides. Sulfuryl chloride (6.28 g, 0.047 mol) was added dropwise to a solution of hexanethiol (5 g, 0.042 mol) in $CH_2Cl_2$ (30 mL) at 0° C. under nitrogen and stirred for 2 h 45 min. $^1H$ NMR ($CDCl_3$): δ 0.90 (t, 3H, J=6.8 Hz), 1.39 (m, 6H), 1.78 (m, 2H), 3.11 (t, 2H, J=7.1 Hz). $^{13}C$ NMR ($CDCl_3$): δ 14.03, 22.52, 27.83, 28.02, 31.31, 41.52.

2,2'-Oxydiethanesulfenyl dichloride. 2-Mercaptoethyl ether (3 g, 0.22 mol) was reacted with a solution of sulfuryl chloride (6.15 g, 0.046 mol) in $CH_2Cl_2$ (30 mL) following the previous procedure. $^1H$ NMR ($CDCl_3$): δ 3.33 (t, 4H, J=6.3 Hz), 3.88 (t, 4H, J=6.2 Hz). $^{13}C$ NMR ($CDCl_3$): δ 40.92, 68.10.

N-Ethylmethyl-hexanesulfenamide (Molecule A). A solution of hexanesulfenyl chloride (6.45 g, 0.042 mol) in $CH_2Cl_2$ (30 mL) was slowly added to a solution of N-ethylmethylamine (7.50 g, 0.13 mol) in $CH_2Cl_2$ (50 mL) at 0° C. under nitrogen and stirred for 7 h. The reaction was diluted with anhydrous $Et_2O$ (130 mL) and washed with saturated NaCl solution in water (3×50 mL). The organic phase was dried over anhydrous magnesium sulfate and evaporated to give a brown oil. The product was isolated by vacuum distillation at 30° C. to yield a colorless oil (3.93 g, 53% yield). $^1$H NMR (CDCl$_3$): δ 0.89 (t, 3H, J=6.8 Hz), 1.14 (t, 3H, J=7.2 Hz), 1.35 (m, 6H), 1.54 (m, 2H), 2.65 (t, 2H, J=7.2 Hz), 2.75 (s, 3H), 2.82 (q, 2H, J=7.1 Hz). $^{13}$C NMR (CDCl$_3$): δ 13.79, 14.09, 22.58, 28.27, 28.89, 31.59, 31.86, 46.82, 53.93. HRMS calculated for C$_9$H$_{21}$NS: 175.1395. Found: 175.1392.

N,N'-Ethylmethyl-bis(2-mercaptoethyl)disulfenamide. A solution of 2,2'-oxydiethanesulfenyl dichloride (4.49 g, 0.022 mol) in CH$_2$Cl$_2$ (30 mL) was reacted with a solution of N-ethylmethylamine (7.70 g, 0.13 mol) in CH$_2$Cl$_2$ (50 mL) following the previous procedure. The extract was filtered through basic alumina to yield a colorless oil (3.29 g, 60% yield). $^1$H NMR (CDCl$_3$): δ 1.13 (t, 6H, J=7.1 Hz), 2.74 (s, 6H), 2.82 (m, 8H), 3.67 (t, 4H, J=7.1 Hz). $^{13}$C NMR (CDCl$_3$): δ 13.70, 32.68, 46.89, 54.13, 70.01. HRMS calculated for C$_{10}$H$_{24}$N$_2$OS$_2$: 252.1321. Found: 252.1324.

N-(Hexanethio)succinimide (Molecule B). 2 Hexanethiol (3 g, 25.37 mmol) was added dropwise to a solution of N-chlorosuccinimide (3.36 g, 26.64 mmol) in CH$_2$Cl$_2$ (70 mL) at 0° C. under nitrogen and stirred for 20 min. The solution changed to a yellow-green color and immediately became cloudy. A solution of triethylamine (2.82 g, 27.91 mmol) in CH$_2$Cl$_2$ (10 mL) was added dropwise to the reaction. After the mixture was stirred for 2.5 h, it was washed with a saturated NaCl solution in water (4×30 mL). The organic layer was dried over anhydrous magnesium sulfate and evaporated to give a colorless oil. The product was isolated by column chromatography using silica gel and 20% ethyl acetate in hexanes to yield a colorless oil (4.73 g, 87% yield). $^1$H NMR (CDCl$_3$): δ 0.88 (t, 3H, J=6.6 Hz), 1.28 (m, 4H), 1.40 (m, 2H), 1.54 (m, 2H), 2.85 (m, 6H). $^{13}$C NMR (CDCl$_3$): δ 13.99, 22.45, 27.90, 28.11, 28.61, 31.28, 37.62, 177.23. HRMS calculated for C$_{10}$H$_{17}$NO$_2$S: 215.0980. Found: 215.0979.

(2,2'-Oxydiethenthio)disuccinimide. 2-Mercaptoethyl ether (10 g, 0.072 mol) was reacted with a solution of N-chlorosuccinimide (20.28 g, 0.15 mol) in CH$_2$Cl$_2$ (300 mL) and a solution of triethylamine (16.10 g, 0.16 mol) in CH$_2$Cl$_2$ (55 mL) following the previous procedure. The mixture was purified by column chromatography using 95% ethyl acetate in hexanes to yield a white solid (11.42 g, 48% yield). $^1$H NMR (CDCl$_3$): δ 2.78 (s, 8H), 2.95 (t, 4H, J=5.9 Hz), 3.68 (t, 4H, J=5.9 Hz). $^{13}$C NMR (CDCl$_3$): δ 28.68, 36.93, 70.90, 177.29. HRMS calculated for C$_{12}$H$_{16}$N$_2$O$_5$S$_2$+Na+: 355.0398. Found: 355.0387.

N,N'-(Hexanethio)disuccinimide. 1,6-Hexanedithiol (7 g, 0.047 mol) was reacted with a solution of N-chlorosuccinimide (13.06 g, 0.098 mol) in CH$_2$Cl$_2$ (230 mL) and a solution of triethylamine (10.37 g, 0.102 mol) in CH$_2$Cl$_2$ (35 mL) following the previous procedure to give a brown solid. The solid was recrystallized from methanol (350 mL) 3 times to yield a white solid (9.90 g, 62% yield). $^1$H NMR (CDCl$_3$): δ 1.47 (m, 8H), 2.83 (m, 12H). $^{13}$C NMR (CDCl$_3$): δ 27.62, 27.65, 28.62, 37.48, 177.26. HRMS calculated for C$_{14}$H$_{20}$N$_2$O$_4$S$_2$+Na$^+$: 367.0762. Found: 367.0757.

N-Benzylmethyl-hexanesulfenamide (Molecule C). N-Benzylmethylamine (1.11 g, 9.19 mmol) was added to a solution of molecule B (1.94 g, 9.01 mmol) in CH$_2$Cl$_2$ (2.5 mL) and stirred at room temperature for 19 h. The reaction was diluted with anhydrous Et$_2$O (30 mL) and washed with water (4×20 mL). The organic phase was dried over anhydrous magnesium sulfate and evaporated to give a yellowish oil (1.7 g, 81% yield). $^1$H NMR (CDCl$_3$): δ 0.89 (t, 3H, J=6.8 Hz), 1.34 (m, 6H), 1.56 (m 2H), 2.69 (m 5H), 4.01 (s, 2H), 7.28 (m, 5H). $^{13}$C NMR (CDCl$_3$): δ 14.07, 22.56, 28.26, 28.80, 31.56, 32.88, 45.97, 65.47, 127.25, 128.23, 128.68, 138.90. HRMS calculated for C$_{14}$H$_{23}$NS: 237.1551. Found: 237.1541.

N-(Propanethio)succinimide. Propanethiol (2.52 g; 33.1 mmol) was slowly added over 10 min to a solution of N-chlorosuccinimide (4.64 g; 34.8 mmol) in 70 mL of CH$_2$Cl$_2$. The reaction was allowed to warm to room temperature and stirred for 2 h. The product was extracted with CH$_2$Cl$_2$ and cleaned by chromatography on silica gel (30% ethyl acetate in hexanes). It was isolated as a white solid (3.00 g; 52% yield). $^1$H NMR (CDCl$_3$): δ 1.02 (t, 3H, J=7.2 Hz), 1.56 (p, 2H, J=7.2 Hz), 2.83 (t, 2H, J=7.2 Hz), 2.85 (s, 4H). $^{13}$C NMR (CDCl$_3$): δ 13.01, 21.54, 28.61, 39.62, 177.19.

Triethylene glycol monomethyl ether tosylate. Tosylchloride (12.6 g, 66 mmol) and triethylamine (10.3 mL, 73 mmol) were combined in a 200 mL round bottom flask with 60 mL of CH$_2$Cl$_2$. Triethylene glycol monomethyl ether (11.4 mL, 73 mmol) was added to this solution at room temperature. The solution was heated to 35° C. in an oil bath for 24 h. The organics were extracted four times with 60 mL of dilute solution and dried with Mg$_2$SO$_4$. Evaporation of the solvent gave a yellow liquid (15. NaHCO$_3$ 0 g, 71% yield). $^1$H NMR (300 MHz, CDCl$_3$): δ 7.80-7.77 (d, 2H), 7.50-7.47 (d, 2H), 4.13-4.10 (t, 2H), 3.59-3.56 (t, 2H), 3.49-3.41 (m, 8H), 3.23 (s, 3H), 2.43 (s, 3H).

(3-Methoxypropyl-(triethylene glycol monomethyl ether) amine (CH$_3$OCH$_2$CH$_2$OCH$_2$CH$_2$OCH$_2$CH$_2$NHCH$_2$CH$_2$CH$_2$OCH$_3$). Triethylene glycol monomethyl ether tosylate (15.0 g, 50 mmol) was added to 100 mL of dry THF in a 200 mL round bottom flask. 3-Methoxypropylamine (12.5 mL, 120 mmol) was added, and the solution was stirred for 96 h at 25° C., then 72 h at 40° C. The THF was evaporated and the remaining organics extracted three times from 100 mL of aqueous NaOH solution with 80 mL of CH$_2$Cl$_2$ and dried with Mg$_2$SO$_4$. A silica gel column (starting at 3% MeOH in CH$_2$Cl$_2$ and ending at 100% MeOH) followed by filtration through a basic alumina plug in hexanes gave a pale yellow liquid (4.4 g, 37% yield). $^1$H NMR (300 MHz, CDCl$_3$): δ 3.67-3.53 (m, 10H), 3.48-3.44 (t, 2H), 3.38 (s, 3H), 3.33 (s, 3H), 2.80-2.77 (t, 2H), 2.72-2.67 (t, 2H), 1.81-1.71 (m, 2H). $^{13}$C NMR (75 MHz, CHCl$_3$): δ 71.79, 71.00, 70.45, 70.33, 70.26, 70.16, 58.73, 58.29, 49.19, 46.91, 30.00.

N-(3-methoxypropyl-(triethylene glycol monomethyl ether)amine-propane sulfenamide. Amine (1.35 g; 5.75 mmol) was added to N-(propanethio)succinimide (0.996 g; 5.75 mmol) dissolved in 2.5 mL of CH$_2$Cl$_2$. The reaction was stirred for 16 h, filtered, and the solvent was removed in vacuo. The product was dissolved in diethylether (10 mL) and washed with water (5 mL). The solvent was removed and the product was clean as judged by $^1$H NMR spectroscopy. It was isolated in 56% yield (0.996 g). $^1$H NMR (CDCl$_3$): δ 0.98 (3H, t, J=7.2 Hz), 1.55 (2H, m), 1.85 (2H, p, J=7.2 Hz), 2.59 (2H, t, J=8 Hz), 2.94 (2H, t, J=7.2 Hz), 3.06 (2H, t, J=6.4 Hz), 3.32 (3H, s), 3.39 (3H, s), 3.41 (2H, t, J=6.4 Hz), 3.55 (2H, m), 3.65 (8H, m). 13C NMR (CDCl$_3$): δ 13.72, 21.36, 28.71, 36.46, 55.58, 58.00, 58.57, 59.03, 69.83, 70.44, 70.45, 70.58, 70.65, 71.98.

Synthesis of Polysulfenamides

Polymer from entry 1 in Table 1. Piperazine (0.176 g, 2.05 mmol) was added to a stirred solution of (2,2'-oxydiethenthio)disuccinimide (0.71 g, 2.05 mmol) in CHCl$_3$ (3.5 mL) and reacted at room temperature for 24 h. The polymer was precipitated into methanol (35 mL) and washed with methanol 3 times. The polymer was dried under vacuum to yield a white powder. $^1$H NMR (CDCl$_3$): δ 2.86 (t, 4H, J=6.8 Hz), 2.97 (s, 8H), 3.65 (t, 4H, J=6.9 Hz). $^{13}$C NMR (CDCl$_3$): δ 32.92, 57.28, 70.10.

Polymer from entry 2 in Table 1. N,N'-(Hexanethio)disuccinimide (3 g, 8.71 mmol) in CHCl$_3$ (19 mL) was reacted with piperazine (0.75 g, 8.71 mmol) following the previous procedure to yield a white powder. $^1$H NMR (CDCl$_3$): δ 1.40 (m, 4H), 1.56 (m, 4H), 2.69 (t, 4H, J=7.5 Hz). $^{13}$C NMR (CDCl$_3$): δ 28.62, 28.82, 32.17, 57.30.

Polymer from entry 3 in Table 1. N,N'-(Hexanethio)disuccinimide (1 g, 2.90 mmol) in CHCl$_3$ (5 mL) was reacted with N,N'-diethylethylenediamine (0.34 g, 2.90 mmol) following the previous procedure. The polymer was precipitated into methanol (10 mL). The polymer was redissolved in a minimal amount of CHCl$_3$ and precipitated into methanol (2 mL) to yield a yellowish oil after drying it under vacuum. $^1$H NMR (CDCl$_3$): δ 1.14 (t, 6H, J=7.1 Hz), 1.40 (m, 4H), 1.54 (m, 4H), 2.60 (t, 4H, J=7.4 Hz), 2.90 (q, 4H, J=7.1 Hz), 3.05 (s, 4H). $^{13}$C NMR (CDCl$_3$): 613.99, 27.92, 28.91, 34.27, 53.23, 56.52.

Polymer from entry 4 in Table 1. (2,2'-Oxydiethenthio)disuccinimide (0.625 g, 1.77 mmol) in CH$_2$Cl$_2$ (1.5 mL) was reacted with N,N'-diethylethylenediamine (0.21 g, 1.77 mmol) following the previous procedure. After evaporating the solvent, the polymer was precipitated into methanol (10 mL) and washed with methanol (15 mL). The polymer was dried under vacuum to yield a yellowish oil. $^1$H NMR (CDCl$_3$): δ 1.14 (t, 6H, J=6.9 Hz), 2.77 (t, 4H, J=7.1 Hz), 2.90 (q, 4H, J=7.0 Hz), 3.04 (s, 4H), 3.65 (t, 4H, J=7.2 Hz). $^{13}$C NMR (CDCl$_3$): δ 14.27, 35.14, 53.66, 56.79, 69.98.

Polymer from entry 5 in Table 1. N,N'-(Hexanethio)disuccinimide (1 g, 2.90 mmol) in CHCl$_3$ (6 mL) was reacted with N,N'-dimethyl-1,6-hexanediamine (0.42 g, 2.90 mmol) following the previous procedure. The polymer was precipitated into methanol (10 mL). The polymer was redissolved in a minimal amount of CHCl$_3$ and precipitated into methanol (7 mL) to yield a yellowish oil after drying it under vacuum. $^1$H NMR (CDCl$_3$): δ 1.31 (m, 4H), 1.41 (m, 4H), 1.55 (m, 8H), 2.64 (t, 4H, J=7.4), 2.76 (m, 10H). $^{13}$C NMR (CDCl$_3$): δ 26.87, 28.18, 28.40, 28.89, 31.68, 47.12, 59.87.

Polymer from a disulfenamide. N,N'-Ethylmethyl-bis(2-mercaptoethyl)disulfenamide (1.34 g, 5.32 mmol) was reacted with N,N'-diethylethylenediamine (0.62 g, 5.32 mmol) in refluxing benzene (5 mL) for 24 h. After evaporating the solvent, the polymer was precipitated into methanol (2×15 mL). The polymer was dried under vacuum to yield a yellowish oil (0.12 g). $^1$H NMR (CDCl$_3$): δ 1.14 (t, 6H, J=6.9 Hz), 2.77 (t, 4H, J=7.1 Hz), 2.90 (q, 4H, J=7.0 Hz), 3.04 (s, 4H), 3.65 (t, 4H, J=7.2 Hz). $^{13}$C NMR (CDCl$_3$): δ 14.27, 35.14, 53.66, 56.79, 69.98.

Kinetic reactions with sulfenamides and thiosuccinimides. Kinetics of molecule A and N-benzylmethylamine (FIG. 1c). Molecule A (71.1 mg, 406 µmol) was dissolved in 1.75 mL of CD$_3$OD and 1 mL (40.7 mg, 232 µmol) of the solution was transferred to a NMR tube. After the addition of N-benzylmethylamine (28.1 mg, 232 µmol), the reaction was monitored by $^1$H NMR spectroscopy.

Kinetics of molecule B and N-benzylmethylamine (FIG. 1d). Molecule B (29.0 mg, 135 µmol) was dissolved in 2 mL of CD$_2$Cl$_2$ and 0.69 mL (10 mg, 46.4 µmol) of the solution was transferred to a NMR tube. N-Benzylmethylamine (37.7 mg, 311 µmol) was dissolved in 2 mL of CD$_2$Cl$_2$, from which 0.30 mL (5.6 mg, 46.4 µmol) was withdrawn and added to the NMR tube. The reaction was monitored by $^1$H NMR spectroscopy.

Kinetics of reaction between N,N'-(hexanethio)disuccinimide and piperazine (FIG. 1e). N,N'-(Hexanethio)disuccinimide (48.4 mg, 141 µmol) was dissolved in 1 mL of CDCl$_3$. Piperazine (12.6 mg, 155 µmol) was added and the reaction was monitored by $^1$H NMR spectroscopy.

Degradation of Sulfenamides

Kinetics of the degradation of molecule C under neutral conditions (FIG. 2a). Molecule C (363.2 mg, 1.53 mmol) was dissolved in 3.3 mL of CD$_3$OD, from which 0.5 mL (55.1 mg, 232 µmol) was transferred to a NMR tube. After adding an additional 0.5 mL of CD$_3$OD, $^1$H NMR spectra were recorded at room temperature every few days. After 33 days, 15% of molecule C degraded to yield N-benzylmethylamine.

This procedure was also followed but the NMR tube was added to a heat bath at 40° C. The reaction showed 27% degradation of molecule C to N-benzylmethylamine after 33 days.

For the kinetics in C$_6$D$_6$ at room temperature, a solution of molecule C (33.9 mg, 143 µmol) in 0.7 mL of C$_6$D$_6$ was added to a NMR tube and $^1$H NMR spectra were recorded every few days for 30 days. The NMR spectra did not change which demonstrated that <3% of molecule C degraded.

Kinetics of the degradation of molecule C with benzoic acid in CD$_3$OD. Molecule C (103.5 mg, 436 µmol) was dissolved in 0.94 mL of CD$_3$OD and 0.5 mL (55.1 mg, 232 µmol) was transferred to a NMR tube. Benzoic acid (202.5 mg, 1.66 mmol) was dissolved in 0.72 mL of CD$_3$OD, from which 0.5 mL (141.8 mg, 1.16 mmol) was withdrawn and added to the NMR tube. The $^1$H NMR spectrum after 4 min showed 51% conversion of molecule C to protonated N-benzylmethylamine. This reaction was too rapid to monitor the kinetics.

Degradation of molecule C with acetic acid in water (FIG. 2b). Acetic acid (0.44 g, 7.37 mmol) was added to a solution of molecule C (0.25 g, 1.05 mmol) in D$_2$O (4 mL) and stirred at room temperature for 41 h. The protonated N-benzylmethylamine was soluble in D$_2$O but the other organic products were not soluble. The reaction was extracted with Et$_2$O (20 mL) and washed with water (4×10 mL). The organic layer was dried over anhydrous magnesium sulfate and evaporated to give a yellowish oil (122 mg). A $^1$H NMR spectrum was obtained of this reaction mixture prior to chromatography to characterize the distribution of products. The products were separated by column chromatography using 4% ethyl acetate in hexanes to give S-hexyl hexanesulfinate (molecule D in FIG. 2b; 84 mg) and a mixture (28 mg) of hexyl disulfide and byproducts. Molecule D was fully characterized as described below.

Molecules E and F were only small components of this reaction mixture and were not obtained in sufficient yield and purity for full characterization. Rather, they were obtained as pure solids from the next reaction described below and were fully characterized at that point. Their presence when molecule C was decomposed with acetic acid was based on their peaks in the $^1$H NMR spectrum which made them simple to identify.

S-hexyl hexanesulfinate (molecule D). $^1$H NMR (CDCl$_3$): δ 0.90 (m, 6H), 1.37 (m, 12H), 1.80 (m, 4H), 3.13 (m, 4H). $^{13}$C NMR (CDCl$_3$): δ 13.97, 14.00, 22.39, 22.48, 23.43, 28.27, 28.28, 30.82, 31.22, 31.32, 32.91, 56.23. HRMS calculated for C$_{12}$H$_{26}$OS$_2$: 250.1425. Found: 250.1416.

Degradation of molecule C with p-toluenesulfonic acid in water. p-Toluenesulfonic acid (0.24 g, 1.24 mmol) was added to a solution of molecule C (0.30 g, 1.24 mmol) in D$_2$O (4 mL) and stirred at room temperature for 16 h. The reaction was extracted with anhydrous Et$_2$O (20 mL) and washed with water (4×10 mL). The organic layer was dried over anhydrous magnesium sulfate and evaporated to give a yellowish oil (116 mg). The distribution of products was checked by $^1$H NMR spectroscopy prior to chromatography. The products were isolated through column chromatography using 4% ethyl acetate in hexanes to give three main products; hexyl disulfide (molecule F in FIG. 2b; 49.1 mg), S-hexyl hexanesulfinate (molecule D in FIG. 2b; 16.4 mg), S-hexyl hexanesulfonate (molecule E in FIG. 2b; 37.3 mg). The $^1$H and $^{13}$C NMR spectra of these compounds matched those reported in the literature and are described below [41, 42].

Hexyl disulfide. $^1$H NMR (CDCl$_3$): δ 0.89 (t, 6H, J=7.0 Hz), 1.48 (m, 12H), 1.67 (m, 4H), 2.68 (t, 4H, J=7.4 Hz). $^{13}$C NMR (CDCl$_3$): δ 14.05, 22.56, 28.23, 29.20, 31.45, 39.21. HRMS calculated for $C_{12}H_{26}S_2$: 234.1476. Found: 234.1469.

S-hexyl hexanesulfonate. $^1$H NMR (CDCl$_3$): δ 0.90 (m, 6H), 1.38 (m, 12H), 1.69 (m, 2H), 1.92 (m, 2H), 3.13 (t, 2H, J=7.4 Hz), 3.29 (t, 2H, J=8). $^{13}$C NMR (CDCl$_3$): δ 13.94, 13.97, 22.32, 22.45, 23.49, 27.66, 28.26, 29.63, 31.15, 31.21, 36.28, 62.71. HRMS calculated for $C_{12}H_{26}O_2S_2$: 266.1374. Found: 266.1367.

Preparation of Microparticles

Blank microparticles were prepared by oil-in-water (o/w) single emulsion, solvent evaporation technique. Briefly, 300 mg of the polymer of entry 2 of Table 1 was dissolved in 3.5 ml of chloroform in a heated water bath at 55° C. This organic phase was then emulsified with 35 ml of 1% (w/v) Mowiol® at 13,500 rpm for 1 min using an IKA Ultra-Turrax T25 basic homogenizer (IKA, Wilmington, N.C.). The mixture was stirred overnight to evaporate the organic phase. The microparticles were then washed three times with deionized water (5000 rpm for 10 min) and lyophilized (Labconco FreeZone 4.5, Kansas City, Mo.). Microparticles were stored at −20° C. until use.

For in vitro particle uptake studies, 2 mg of Rhodamine B (Sigma, St. Louis, Mo.) was dissolved along with the polysulfenamide in chloroform prior to the formation of the oil-in-water single emulsion. The rhodamine labeled particles were washed and collected as described above.

Surface morphology. Microparticle morphology was assessed by scanning electron microscopy (SEM, Hitachi S-4000). Air-dried microparticles were placed on silicon wafers mounted on SEM specimen stubs. The stubs were coated with ~5 nm of gold by ion beam evaporation followed by imaging using SEM operated at 3 kV accelerating voltage.

Particle size and zeta potential. Microparticle size and zeta potential was measured using the Zetasizer Nano ZS (Malvern, Southborough, Mass.). The microparticles were suspended in deionized water at a concentration of 1 mg ml$^{-1}$. The zeta potential was measured using folded capillary cell in automatic mode and the size was measured using a disposable sizing cuvette (DTS0012). The size was measured at 25° C. at a 173° scattering angle.

Crosslinking with polyethylene imine (PEI). PEI crosslinking was carried out by adding PEI into a suspension of microparticles in deionized water (1 mg ml$^{-1}$). The solution was vortexed for 30 sec and left at 4° C. for 5 h. The microparticles were washed with deionized water and collected by centrifugation (7000 rpm for 10 min). The zeta potential of the crosslinked particles was measured as described above.

Degradation of Microparticles in Aqueous Buffer

For in vitro analysis, about 85 mg of the microparticles was suspended in either phosphate buffer saline (PBS, pH 7.4) or acetate buffer (pH 4). The samples were agitated at 37° C., 150 rpm in a horizontal shaker (C24 incubator shaker, New Brunswick Scientific, Edison, N.J.). At specific time points, the samples were centrifuged for 10 min at 7000 rpm. The pellet was washed three times with deionized water and lyophilized. The dry weight of the pellet was recorded and percentage weight loss was calculated for each sample. In addition, the samples were also analyzed by scanning electron microscopy to observe change in surface morphology of microparticles.

Microparticle Uptake into Cells and In Vitro Toxicity

Particle uptake into cells. Uptake of rhodamine labeled microparticles was studied in JAWSII cells and HEK293 cells. Chambers were initially coated with 300 μl of poly L-lysine (0.1% w/v) overnight. Following coating, ~1×10$^4$ cells were seeded per well and incubated overnight at 37° C. in a humidified 5% $CO_2$-containing atmosphere. Rhodamine labeled particles were added to the media at a concentration of 50 micrograms per well. The particles were incubated with the cells for about 18 h. Cells were washed three times with sterile PBS and fixed with 4% paraformaldehyde. The nucleus was stained with DAPI. Vectashield® mounting medium was added onto slide and sealed with coverslip. The samples were imaged using LSM710 confocal microscope (Carl Zeiss MicroImaging, Thornwood, N.Y.).

In vitro cytotoxicity evaluation of microparticles. The cytotoxicity of polymer microparticles was evaluated using the MTS assay. HEK293 cells were seeded in a 96 well plate at a density of 1×10$^4$ cells/well and incubated for 24 hours at 37° C. in a humidified 5% $CO_2$-containing atmosphere. Following this, the cells were incubated with 200 μl of complete DMEM containing various concentrations of microparticles. The particles were incubated at 4 h and 24 h to study the time dependent effect on toxicity of the microparticles. MTS solution in PBS was added to each well and incubated for 4 h. The optical density of the sample was measured at 490 nm using a Spectramax® Plus microplate spectrophotometer (Molecular Device, California). The values obtained for cell viability represent the average of eight values. Cell viability (%) was calculated as [(mean absorbance of the sample−reference absorbance])/mean absorbance of the control]×100.

In Vivo Toxicity of Polysulfenamides in Mice

Mice. BALB/c male mice between 6-8 weeks of age were obtained from Jackson Laboratories (Bar Harbor, Me., USA) and maintained in filtered cages. All mice were housed in the University of Iowa Animal Facility (Iowa City, Iowa), an Association for Assessment and Accreditation of Laboratory Animal Care International-approved facility. All experiments were conducted in accordance with guidelines and regulations approved by the University of Iowa Institutional Animal Care and Use committee.

Figure 6:
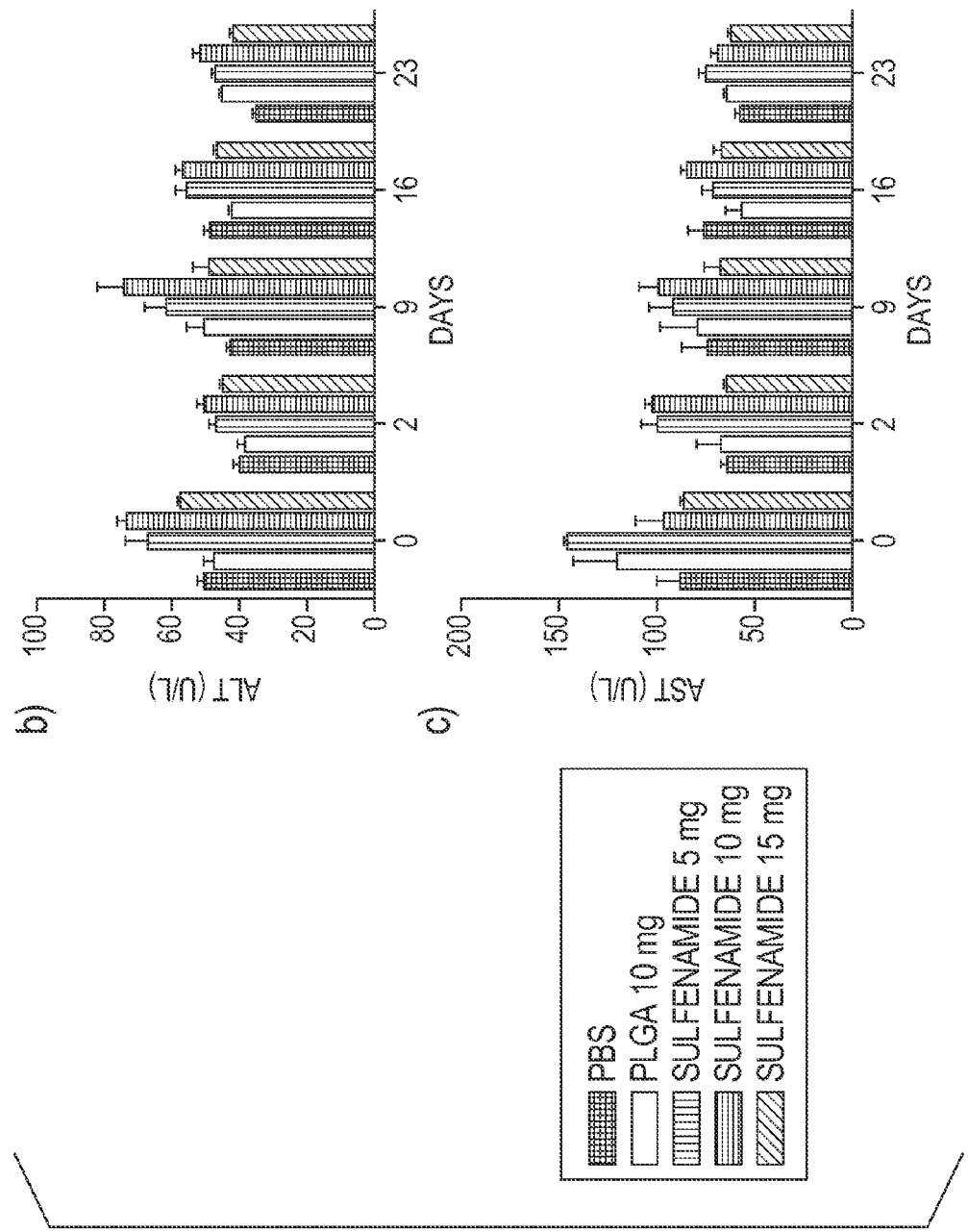
FIG. 6 illustrates in vivo ALT and AST levels in BALB/c mice following intraperitoneal injection of microparticles (n=4 and samples processed in triplicate).

In vivo microparticle treatment and controls groups. Mice were divided into groups of five, each containing 4 replicates. All the groups were bled and sera isolated (as described below) prior to administration of treatments and controls (day 0) to evaluate the initial ALT and AST levels in mice under normal conditions. The treatment groups consisted of polysulfenamide MPs injected intraperitoneally (i.p.) as a suspension in 300 μL sterile PBS (1×) in amounts of 5 mg, 10 mg and 15 mg along with 10 mg of poly(D,L-lactide-co-glycolide) (PLGA) as a positive control group. An additional control group received sterile PBS given i.p. The sera were again harvested from each group at predetermined time intervals (days 2, 9, 16 and 23) after treatment with MPs and analyzed for serum transaminase activity (ALT and AST levels) to characterize and determine any hepatotoxicity triggered as a result of the MPs. Mice were also monitored daily using the body scoring technique. The results are shown in FIG. 6.

Isolation of mice sera. The mice were anesthetized by i.p. administration of ketamine-xylazine mixture (100 μl/20 g mouse body weight). About 200 μl of whole blood was collected from each mouse by puncturing the submandibular vein with a 5-mm Golden Rod animal lancet (Medipoint, Mineola, N.Y.) into Eppendorf microcentrifuge tubes. The collected blood was allowed to incubate at room temperature for 2 h. After removal of the blood clot, samples were centrifuged at 4° C. for 10 min at 3000×g. The sera obtained was transferred to new tubes and stored at −80° C. until further analysis. Sera were mixed with ALT or AST assay solution and then measured in a spectrophotometer (using the Vitros® 350 analyzer, Ortho Clinical Diagnostics, New Jersey) following the supplier's protocol.

Statistical analysis. Group data are reported as mean+/− SD. Differences between groups were analyzed by two-tailed unpaired t test. Levels of significance were accepted at the $P<0.05$ level. Statistical analyses were performed using Prism 3.02 software (Graphpad Software, Inc., San Diego, Calif.). A paired t-test was conducted to determine any significant increase in serum ALT and AST levels relative to day 0 ($p<0.05$). All in vivo toxicity data reported are means±SEM, unless otherwise noted. The graphs on in vivo toxicity were generated using GraphPad Prism 5 and the statistical analyses were conducted using R.

REFERENCES

1 Nguyen, D. N., Green, J. J., Chan, J. M., Langer, R., Anderson, D. G., (2009) Polymeric materials for gene delivery and DNA vaccination. Adv. Mater. 21:847-867.
2 Twaites, B., de las Heras Alarcon, C., Alexander, C., (2005) Synthetic polymers as drugs and therapeutics. J. Mater. Chem. 15:441-445.
3 Green, J. J., Langer, R., Anderson, D. G., (2008) A combinatorial polymer library approach yields insight into non-viral gene delivery. Accts. Chem. Res. 41:749-759.
4 Cao, J., Langer, R., (2010) Nanotechnology in drug delivery and tissue engineering: from discovery to applications. Nano Lett. 10:3223-3230.
5 Jabbari, E., Lu, L., Yaszemski, M. J., (2006) Synthesis and characterization of injectable and biodegradable composites for orthopedic applications. Handbook of biodegradable polymeric materials and their applications 2:239-270.
6 Peter, S. J., Miller, M. J., Yasko, A. W., Yaszemski, M. J., Mikos, A. G., (1998) Polymer concepts in tissue engineering. J. Biomed. Mater. Res. 43:422-427.
7 Anderson, D. G., Nurdick, J. A., Langer, R., (2004) Materials science: Smart biomaterials. Science 305:1923-1924.
8 Ciuffarin, E., Gambarotta, S., Isola, M., Senatore, L., (1978) Chemistry of sulphenates in acidic media. J. C. S. Perkin II 554-557.
9 Saito, G., Swanson, J. A., Lee, K.-D., (2003) Drug delivery strategy utilizing conjugation via reversible disulfide linkages: role and site of cellular reducing activities. Adv. Drug Delivery Rev. 55:199-215.
10 Mohanad, M., Dixon, A. S., Lim, C. S., (2010) Controlling subcellular delivery to optimize therapeutic effect. Therapeutic Del. 1:169-193.
11 Meng, H. X., M. et al., (2010) Autonomous in vitro anticancer drug release from mesoporous silican nanoparticles by pH-sensitive nanovalves. J. Am. Chem. Soc. 132: 12690-12697.
12 Arima, H., Motoyama, K., (2009) Recent findings concerning PAMAM dendrimer conjugates with cyclodextrins as carriers of DNA and RNA. Sensors 9:6346-6361.
13 Oh, K. T., Yin, H., Lee, E. S., Bae, Y. H., (2007) Polymeric nanovehicles for anticancer drugs with triggering release mechanisms. J. Mater. Chem. 17:3987-4001.
14 Kroeze, R. J., Helder, M. N., Govaert, L. E., Smit, T. H., (2009) Biodegradable polymers in bone tissue engineering. Materials 2:833-856.
15 Kohane, D. S., Langer, R., (2010) Biocompatibility and drug delivery systems. Chem. Sci. 1:441-446.
16 Williams, C. K., (2007) Synthesis of functionalized biodegradable polyesters. Chem. Soc. Rev. 36:1573-1580.
17 Vert, M., (2009) Degradable and bioresorbable polymers in surgery and pharmacology: beliefs and facts. J. Mater. Sci.: Mater. Med. 20:437-446.
18 Kwon, G. S., Furgeson, D. Y., (2007) Biodegradable polymers for drug delivery systems. Biomedical polymers: 83-110.
19 Koval, I. V., (1996) Synthesis and applications of sulfenamides. Russian Chem. Rev. 65:421-440.
20 Matsuo, J.-I., Kawana, A., Yamanaka, H., Mukaiyama, T., (2003) Sulfenamide-catalyzed oxidation of primary and secondary alcohols with molecular bromine. Chem. Lett. 32:182-183.
21 Guarino, V. R., Karunaratne, V., Stella, V. J., (2007) Sulfenamides as prodrugs of NH-acidic compounds: A new prodrug option for the amide bond. Bioorg. Med. Chem. Lett. 17:4910-4913.
22 Knapp, S., Darout, E., Amorelli, B., (2006) New glycomimetics: Anomeric sulfonates, sulfenamides, and sulfonamides. J. Org. Chem. 71:1380-1389.
23 Craine, L., Raban, M., (1989) The chemistry of sulfenamides. Chem. Rev. 89:689-712.
24 Capozzi, G., Modena, G., Pasquato, L., The chemistry of sulphenic acids and their derivatives. (John Wiley & Sons, New York, 1990).
25 Lopez, M., Drilland, N., Bornaghi, L. F., Poulsen, S.-A., (2009) Synthesis of S-glycosyl primary sulfonamides. J. Org. Chem. 74:2811-2816.
26 Owen, D. J. et al., (2007) Synthesis and evaluation of galactofuranosyl N,N-dialkyl sulfenamides and sulfonamides as antimycobacterial agents. Bioorg. Med. Chem. Lett. 17:2274-2277.
27 Kice, J. L., (1980) Mechanisms and reactivity in reactions of organic oxyacids of sulfur and their anhydrides. Adv. Phys. Org. Chem. 17:65-181.
28 Nagy, P., Ashby, M. T., (2007) Reactive sulfur species: kinetics and mechanism of the hydrolysis of cysteine thiosulfinate ester. Chem. Res. Toxicol. 20:1364-1372.
29 Freeman, F., Kodera, Y., (1995) Garlic chemistry: stability of S-(2-propenyl) 2-propene-1-sulfinothioate (allicin) in blood, solvents, and simulated physiological fluids. J. Agric. Food Chem. 43:2332-2338.
30 Nagy, P., Ashby, M. T., (2005) Reactive sulfur species: kinetics and mechanism of the oxidation of cystine by hypochlorous acid to give N,N'-dichlorocystine. Chem. Res. Toxicol. 18:919-923.
31 Kice, J. L., Rogers, T. E., (1974) Mechanism of the alkaline hydrolysis of aryl thiolsulfinates and thiolsulfonates. J. Am. Chem. Soc. 96:8009-8014.
32 Buncel, E., Um, I.-H., (2004) The a-effect and its modulation by solvent. Tetrahedron 60:7801-7825.
33 Anslyn, E. V., Dougherty, D. A., Modern physical organic chemistry. (University Science Books, Sausalito, Calif., 2006).
34 Hemenway, J. N., Nti-Addae, K., Guarino, V. R., Stella, V. J., (2007) Preparation, characterization, and in vivo conversion of new water-soluble sulfenamide prodrugs of carbamazepine. Bioorg. Med. Chem. Lett. 17:6629-6632.
35 Lee, S. S., Hughes, P., Ross, A. D., Robinson, M. R., (2010) Biodegradable implants for sustained drug release in the eye. Pharma. Research 27:2043-2053.

36 Gaucher, G., Marchessault, R. H., Leroux, J.-C., (2010) Polyester-based micelles and nanoparticles for the parenteral delivery of taxanes. J. Controlled Release 143: 2-12.
37 Malyala, P., O'Hagan, D. T., Singh, M., (2009) Enhancing the therapeutic efficacy of CpG oligonucleotides using biodegradable microparticles. Adv. Drug Delivery Rev. 6:218-225.
38 Elfinger, M., Uezguen, S., Rudolph, C., (2008) Nanocarriers for gene delivery—polymer structure, targeting ligands, and controlled-release devices. Curr. Nanoscience 4:322-353.
39. Branchaud, B. P. Studies on the preparation and reactions of tritylsulfenimines J. Org. Chem. 48, 3531-3538 (1983)
40. Henke, A.; Srogl, J. Thioimides: new reagents for effective synthesis of thiolesters from carboxylic acids J. Org. Chem. 73, 7783-7784 (2008).
41. Freeman, F., Keindl, M. C. A facile synthesis of symmetrical alkanesulfonothioic S-alkyl esters (S-alkyl alkanethiosulfonates) Synthesis 913-915, (1983).
42. Freeman, F., Angeletakis, C. N. Carbon-13 nuclear magnetic resonance study of the conformations of disulfides and their oxide derivatives J. Org. Chem. 47, 4194-4200 (1982).
43. Freeman, F., Angeletakis, C. N., Maricich, T. J. $^1$H NMR and $^{13}$C NMR spectra of Disulfides, Thiosulfinates and Thiosulfonates Org. Magn. Reson. 17, 53-58 (1982).
44 T. W. Greene, P. G. M. Wuts, Protective groups in organic synthesis, John Wiley & Sons, Inc., New York, 1991.
45 F. Zhao, W. Bi, S. Zhao, J. Macromolecular Sci. B: Physics 2011, 50, 1460-1469; Z. Wang, H. Zhao, J. Zhao, X. Wang, J. Appl. Polym. Sci. 2010, 117, 2523-2529; R. Guo, A. G. Talma, R. N. Datta, W. K. Dierkes, J. W. M. Noordermeer, Eur. Poly. J. 2008, 44, 3890-3893.
46 W.-L. Man, W. W. Y. Lam, H.-K. Kwong, S.-M. Peng, W.-T. Wong, T.-C. Lau, Inorg. Chem. 2010, 49, 73-81.
47 M. H. V. Huynh, P. S. White, T. J. Meyer, Angew. Chem. Int. Ed. 2000, 39, 4101-4104; M. H. V. Huynh, D. E. Morris, P. S. White, T. J. Meyer, Angew. Chem. Int. Ed. 2002, 41, 2330-2333.
48 M. Lopez, N. Drilland, L. F. Bornaghi, S.-A. Poulsen, J. Org. Chem. 2009, 74, 2811-2816.
49 T. Mukaiyama, J.-I. Matsuo, D. Iida, Kitagawa, Chem. Lett. 2001, 30, 846-847; Y. Matsumoto, A. Kawana, Y. Hiroyuki, T. Mukaiyama, Chem. Lett. 2003, 32, 182-183.
50 I. V. Koval, Russian Chem. Rev. 1996, 65, 421-440; V. R. Guarino, V. Karunaratne, V. J. Stella, Bioorg. Med. Chem. Lett. 2007, 17, 4910-4913; L. Craine, M. Raban, Chem. Rev. 1989, 89, 689-712.
51 J.-I. Matsuo, A. Kawana, H. Yamanaka, T. Mukaiyama, Chem. Lett. 2003, 32, 182-183; S. Knapp, E. Darout, B. Amorelli, J. Org. Chem. 2006, 71, 1380-1389; G. Capozzi, G. Modena, L. Pasquato, The chemistry of sulphenic acids and their derivatives, John Wiley & Sons, New York, 1990.
52 J. Intra, A. K. Salem, J. Controlled Release 2008, 130, 129-138; X. Q. Zhang, C. E. Dahle, G. J. Weiner, A. K. Salem, J. Pharmaceutical Sci. 2007, 96, 3283-3292.
53 M. H. Ullman-Cullere, C. J. Foltz, Lab. Animal Sci. 1999, 49, 319-323.

The invention claimed is:
1. A method of manufacturing a polysulfenamide, comprising:
forming a mixture comprising an activated dithiol and a secondary diamine.

2. The method of claim 1, wherein the activated dithiol is of formula (3):

$$X\!-\!S\!-\!R^1\!-\!S\!-\!X \quad\quad (3),$$

wherein $R^1$ is selected from a group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl, and X is selected from a group consisting of halogen, tosylate group, mesylate group, succinimidyl group, and imidyl group.

3. The method of claim 2, wherein X is a succinimidyl group.

4. The method of claim 1, wherein the mixture further comprises a solvent selected from a group consisting of methylene chloride ($CH_2Cl_2$), chloroform ($CHCl_3$), $CCl_4$, hexane, benzene, toluene, 1,4-dioxane, diethyl ether, tetrahydrofuran, ethyl acetate, acetone, dimethylformamide, acetonitrile, dimethyl sulfoxide, or a combination thereof.

5. The method of claim 1, wherein the secondary diamine is a secondary diamine of formula (2):

wherein $R^4$, $R^5$, and $R^6$ are each independently selected from a group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

6. The method of claim 5, wherein $R^4$, $R^5$, and $R^6$ are each independently selected from a group consisting of alkyl and ether.

7. The method of claim 5, wherein $R^5$ and $R^6$ are part of the same cyclical moiety.

8. A polysulfenamide comprising a repeating unit of formula (4):

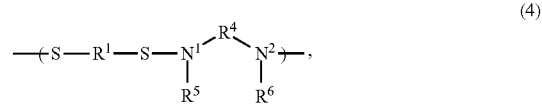

wherein $R^1$ is selected from a group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl, and $R^4$, $R^5$, and $R^6$ are each independently selected from a group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

9. The polysulfenamide of claim 8, wherein $R^1$ is selected from a group consisting of alkyl, cycloalkyl, ether, and cycloether.

10. The polysulfenamide of claim 8, wherein $R^4$, $R^5$, and $R^6$ are each independently selected from a group consisting of alkyl and ether.

11. The polysulfenamide of claim 8, wherein $R^5$ and $R^6$ are part of the same cyclic moiety.

12. A microparticle comprising a polysulfenamide, wherein the microparticle has an average size of about 0.1 μm to about 20 μm.

13. The microparticle of claim 12, wherein the microparticle has an average size of about 1 μm to about 5 μm.

14. The microparticle of claim 12, wherein the microparticle has an average size of about 2 μm to about 3 μm.

15. The microparticle of claim 12, wherein the microparticle is further functionalized with an amine.

16. The microparticle of claim 12, wherein the polysulfenamide comprises a repeating unit of formula (4):

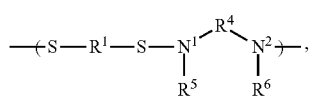

(4)

wherein $R^1$ is selected from a group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl, and $R^4$, $R^5$, and $R^6$ are each independently selected from a group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

17. The microparticle of claim 16, wherein the microparticle is further functionalized with an amine.

18. A method of manufacturing a polysulfenamide, comprising:
    forming a mixture comprising a disulfenamide and a secondary diamine.

19. The method of claim 18, wherein the disulfenamide is of formula (1):

(1), wherein $R^1$ is selected from a group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl, and $R^2$, $R^3$, $R^{2'}$, and $R^{3'}$ are each independently selected from a group consisting of hydrogen, alkyl, alkenyl, alkynyl, haloalkyl, alkoxyalkyl, hydroxyalkyl, cycloalkyl, ether, aryl, and heteroaryl.

20. The method of claim 18, wherein the secondary diamine is a secondary diamine of formula (2):

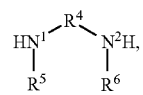

(2)

wherein $R^4$, $R^5$, and $R^6$ are each independently selected from a group consisting of alkyl, alkenyl, alkynyl, haloalkyl, alkoxyalkyl, hydroxyalkyl, ether, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

* * * * *

UNITED STATES PATENT AND TRADEMARK OFFICE
CERTIFICATE OF CORRECTION

| | | |
|---|---|---|
| PATENT NO. | : 9,345,776 B2 | |
| APPLICATION NO. | : 13/984228 | |
| DATED | : May 24, 2016 | |
| INVENTOR(S) | : Ned B. Bowden et al. | |

It is certified that error appears in the above-identified patent and that said Letters Patent is hereby corrected as shown below:

In the Specification

Column 1, Lines 12-16, please delete "This invention was made with government support under CA128414, and CA013345 awarded by the National Institutes of Health, contract CHE-0848162 awarded by the National Science Foundation, and under contracts 1R21CA13345-01/1R21CA128414-01A2 awarded by the National Institutes of Health. The government has certain rights in the invention." and insert -- This invention was made with government support under CA128414, and CA013345 awarded by the National Institutes of Health, and CHE0848162 awarded by the National Science Foundation. The government has certain rights in the invention. -- therefor.

Signed and Sealed this
Thirty-first Day of October, 2023

Katherine Kelly Vidal
*Director of the United States Patent and Trademark Office*